(12) United States Patent
He et al.

(10) Patent No.: US 12,343,433 B2
(45) Date of Patent: Jul. 1, 2025

(54) MICROENCAPSULATION METHOD FOR IMPROVING STABILITY OF ANTHOCYANIN, PRODUCT THEREFROM AND USE THEREOF

(71) Applicant: WUHAN POLYTECHNIC UNIVERSITY, Hubei (CN)

(72) Inventors: Jingren He, Hubei (CN); Lan Zhou, Hubei (CN); Rui Zhang, Hubei (CN); Ying Mao, Hubei (CN); Ning Yang, Hubei (CN); Shuyi Li, Hubei (CN); Yi He, Hubei (CN); Zhenzhou Zhu, Hubei (CN)

(73) Assignee: WUHAN POLYTECHNIC UNIVERSITY, Wuhan (CN)

( * ) Notice: Subject to any disclaimer, the term of this patent is extended or adjusted under 35 U.S.C. 154(b) by 833 days.

(21) Appl. No.: 17/503,351

(22) Filed: Oct. 17, 2021

(65) Prior Publication Data
US 2022/0071914 A1   Mar. 10, 2022

Related U.S. Application Data

(63) Continuation of application No. PCT/CN2020/084963, filed on Apr. 15, 2020.

(30) Foreign Application Priority Data

Apr. 17, 2019 (CN) .......................... 201910309622.5

(51) Int. Cl.
| | | |
|---|---|---|
| *A61K 9/50* | (2006.01) | |
| *A23L 5/43* | (2016.01) | |
| *A23L 29/00* | (2016.01) | |
| *A23L 29/256* | (2016.01) | |
| *A23P 10/35* | (2016.01) | |
| *A61K 47/22* | (2006.01) | |
| *B01D 15/20* | (2006.01) | |
| *B01D 15/42* | (2006.01) | |
| *B01D 61/02* | (2006.01) | |
| *B01D 61/04* | (2006.01) | |
| *B01D 61/14* | (2006.01) | |
| *B01D 61/16* | (2006.01) | |
| *B01D 61/58* | (2006.01) | |
| *B01D 69/02* | (2006.01) | |

(52) U.S. Cl.
CPC .............. *A61K 9/5089* (2013.01); *A23L 5/43* (2016.08); *A23L 29/015* (2016.08); *A23L 29/035* (2016.08); *A23L 29/256* (2016.08); *A23P 10/35* (2016.08); *A61K 9/5036* (2013.01); *A61K 47/22* (2013.01); *B01D 15/203* (2013.01); *B01D 15/426* (2013.01); *B01D 61/025* (2013.01); *B01D 61/027* (2013.01); *B01D 61/04* (2013.01); *B01D 61/145* (2013.01); *B01D 61/147* (2013.01); *B01D 61/149* (2022.08); *B01D 61/16* (2013.01); *B01D 61/58* (2013.01); *B01D 69/02* (2013.01); *A23V 2002/00* (2013.01); *B01D 2311/04* (2013.01); *B01D 2311/06* (2013.01); *B01D 2311/2626* (2013.01); *B01D 2311/2649* (2013.01); *B01D 2311/2676* (2013.01)

(58) Field of Classification Search
CPC .... A23L 29/015; A23L 29/035; A23L 29/256; A23L 33/105; A23L 5/43; A23P 10/35; A23V 2002/00; A61K 31/352; A61K 47/22; A61K 9/501; A61K 9/5015; A61K 9/5036; A61K 9/5089
See application file for complete search history.

(56) References Cited

FOREIGN PATENT DOCUMENTS

| | | |
|---|---|---|
| CN | 103271424 A | 9/2013 |
| CN | 106589402 A | 4/2017 |
| CN | 108850790 A | 11/2018 |
| CN | 110013034 A | 7/2019 |
| KR | 101317379 B1 * | 10/2013 |

OTHER PUBLICATIONS

Lim et. al., KR 101317379 B1, publ., Oct. 11, 2013, English translation (Year: 2013).*
Li et. al., Recent Advances of the stability of anthocyanins, publ. 2009, English translation (Year: 2009).*
Li Yingchang, et al.Research advances of the stability of anthocyanins,China Condiment,Dec. 31, 2009, 34(011):pp. 88-90 and 111.

* cited by examiner

*Primary Examiner* — Sarah Pihonak

(57) ABSTRACT

The present invention discloses a microencapsulation method for improving stability of anthocyanin, a product therefrom and use thereof. A preparation method of anthocyanin microcapsules includes: (1) taking sodium alginate as a wall material, adding sodium alginate and calcium carbonate into water, and swelling for 1-2 h to obtain a wall material gel system; (2) taking anthocyanin prepared by a special process as a core material, and fully and uniformly mixing the wall material gel system with an anthocyanin solution to obtain a water phase; (3) mixing Span80 and vegetable oil to obtain an oil phase, mixing the water phase with the oil phase, and magnetically stirring for emulsifying to obtain a W/O emulsion; and (4) adjusting the pH of the W/O emulsion to be acidic, mixing the W/O emulsion with a salt buffer solution, standing for 1-2 h, and then separating the oil phase and the water phase.

8 Claims, 10 Drawing Sheets

MICROENCAPSULATION METHOD FOR IMPROVING STABILITY OF ANTHOCYANIN, PRODUCT THEREFROM AND USE THEREOF

CROSS-REFERENCE TO RELATED APPLICATIONS

This application is a continuation of International Patent Application No. PCT/CN2020/084963, filed on Apr. 15, 2020, which claims the benefit of priority from Chinese Patent Application No. 201910309622.5, filed on Apr. 17, 2019. The content of the aforementioned application, including any intervening amendments thereto, is incorporated herein by reference in its entirety.

TECHNICAL FIELD

The present invention relates to the field of preparation of pigments, in particular to a microencapsulation method for improving the stability of anthocyanin, a product therefrom and use thereof.

BACKGROUND OF THE PRESENT INVENTION

Anthocyanin is a water-soluble natural colorant, which has antioxidant, anti-inflammatory and other biological activities and great application potential in food and other fields, but has relatively poor stability due to susceptibility to temperature, light and other factors. Therefore, an encapsulation technology is adopted to improve the stability of anthocyanin and expand the application scope.

At present, common methods for the microencapsulation of anthocyanin include the spray drying method, the liposome method and the coacervation method. The spray drying method is the most commonly used encapsulation technology in food industry. During spray drying, a solvent evaporates rapidly, and active ingredients are instantly retained to form an amorphous solid dispersion. The method is simple in process, low in cost, and suitable for temperature-sensitive active substances. The spray drying method has been proved to be effective in protecting polyphenol compounds, but may degrade heat-sensitive anthocyanin to a certain extent at high temperature.

Therefore, it is necessary to provide a microencapsulation method with simple process and low cost and capable of keeping the structural stability of anthocyanin at high temperature.

SUMMARY OF THE PRESENT INVENTION

To solve the above technical problems, the present invention provides a microencapsulation method for improving the stability of anthocyanin, a product therefrom and use thereof. The anthocyanin is prepared by a special preparation process to improve the yield and purity of anthocyanin. Meanwhile, the microencapsulation method of anthocyanin is optimized by improved process parameters, to ensure the structural stability of anthocyanin and reduce the cost.

To achieve the purposes and other advantages according to the present invention, on one hand, the present invention provides a microencapsulation method for improving the stability of anthocyanin, including the following steps:

S1, taking sodium alginate as a wall material, respectively preparing sodium alginate, calcium carbonate and water according to a weight ratio of sodium alginate to calcium carbonate to water of (2-4):1:(15-25), and then adding the sodium alginate and the calcium carbonate into water to swell for 1-2 h to obtain a wall material gel system;

S2, taking anthocyanin as a core material, and fully and uniformly mixing the wall material gel system with an anthocyanin solution for later use at a weight ratio of the sodium alginate to the anthocyanin of (12-20):1 to obtain a water phase;

S3, mixing Span80 with vegetable oil at a volume ratio of (1-2):1 to obtain an oil phase, mixing the water phase with the oil phase at a volume ratio of (3-5):1, and magnetically stirring the mixture for emulsifying to obtain a W/O emulsion; and S4, adjusting the pH of the W/O emulsion to be acidic, mixing the W/O emulsion with a buffer solution at a volume ratio of 1:(3-5), standing for 1-2 h, and separating the oil phase from the water phase to obtain a liquid anthocyanin microcapsule.

Preferably, in the step S1, the weight ratio of the sodium alginate to the calcium carbonate to the water is 3:1:20.

Preferably, in the step S2, the weight ratio of the sodium alginate to the anthocyanin is 15:1.

Preferably, in the step S3, the volume ratio of the water phase to the oil phase is 4:1.

Preferably, in the step S4, the step of adjusting the pH of the W/O emulsion to be acidic includes: adding the vegetable oil containing an acidic solution into the W/O emulsion, wherein a weight ratio of the acidic solution to calcium carbonate is 3:1.

Preferably, in the step S4, the buffer solution is a phosphate buffer solution containing NaCl with a mass concentration of 0.9%.

Preferably, the microencapsulation method for improving the stability of anthocyanin further includes a step S5 of spray-drying the liquid anthocyanin microcapsule to obtain anthocyanin microcapsule powder under the conditions that the heater temperature is 100-130° C., the feed rate is 10-15 r/min, and the vacuum pressure is 0.02-0.05 MPa.

Preferably, in the step S2, the anthocyanin is prepared by the following processes:

S21, drying and crushing raw materials for extracting the anthocyanin, and sieving the obtained raw materials with a 200-300-mesh sieve to obtain raw material powder;

S22, mixing the raw material powder with an extracting solution uniformly at a weight-volume ratio of 1:(15-20); then adding a compound enzyme accounting for 0.02-0.03% by weight of the raw material powder to obtain an extraction system; performing ultrasonic extraction at 35-45° C. in the extraction system for 60-90 min, wherein the extracting solution includes 70-75% of ethanol with a volume fraction of 85%, 2-4% of acetic acid with a volume fraction of 5%, 10-12% of sucrose and 10-12% of choline chloride by weight, the ultrasonic power in the ultrasonic extraction is 200-400 W, the compound enzyme is composed of cellulase, pectinase and amylase based on weight parts, and the weight ratio of cellulase to pectinase to amylase is 1:1:1.5; and performing solid-liquid separation after the ultrasonic extraction to obtain a first filter residue and a first filtrate;

S23, adding 85% ethanol and 3% citric acid solution, which are 5-8 times the weight of the first filter residue and 0.2-0.3 time the weight of the first filter residue respectively, into the first filter residue, performing ultrasonic extraction at 35-45° C. for 45-60 min, and performing solid-liquid separation after the ultrasonic extraction to obtain a second filter residue and a second filtrate;

S24, combining the first filtrate with the second filtrate to obtain a crude extract, centrifuging the crude extract at 8000-10000 rpm for removing precipitates to obtain a refined extract, and sequentially filtering the refined extract through a microfiltration membrane with an aperture of 2-5 μm, an ultrafiltration membrane with an aperture of 0.02-0.05 μm and a nanofiltration membrane with an aperture of 0.001-0.002 μm to obtain an extracted clear solution, wherein the filtration pressure is 0.2-0.4 MPa and the filtration temperature is 25-35° C. when the refined extract is filtered through the microfiltration membrane with the aperture of 2-5 μm and the ultrafiltration membrane with the aperture of 0.02-0.05 μm; and the filtration pressure is 1.5-2.0 MPa and the filtration temperature is 25-35° C. when the refined extract is filtered through the nanofiltration membrane with the aperture of 0.001-0.002 μm;

S25, adding 85% ethanol, which is 1-2 times the volume of the extracted clear Solution, into the extracted clear solution, centrifuging at 12000 rpm for 15 min, making the supernatant obtained after discarding precipitates pass through a column filled with XAD-7HP macroporous adsorption resin, wherein a volume ratio of the supernatant to the column is 3:1, eluting the macroporous adsorption resin with 5% ethanol to remove impurities after the macroporous adsorption resin forms a saturated uniform color band, then desorbing a pigment adsorbed by the macroporous adsorption resin with 1-2 column volumes of 70% acidic ethanol until the macroporous adsorption resin is colorless, and collecting eluent;

S26, concentrating the eluent by a high-pressure reverse osmosis membrane after passing through the ultrafiltration membrane with the aperture of 0.02-0.05 am, to obtain an intercepted concentrated solution with a solid content of 15-25%, wherein the interception molecular weight of the high-pressure reverse osmosis membrane is 200 Da, the concentration temperature is 25-35° C., and the pressure is 3.0-4.5 MPa during concentration by the high-pressure reverse osmosis membrane;

S27, concentrating the intercepted concentrated solution under vacuum and reduced pressure at 35-55° C. until ethanol is completely removed, to obtain a concentrated solution with a Baume degree of 3-5°; and S28, adding 10% acetic acid, which is 4-5% by volume of the concentrated solution, into the concentrated solution, heating at 30-40° C. for 30 min, rapidly freezing at −70° C., and then freeze-drying to obtain the anthocyanin.

On the other hand, the present invention also provides an anthocyanin microcapsule product prepared by the microencapsulation method.

On the other hand, the present invention also provides use of the anthocyanin microcapsule product in the preparation of food, healthcare products, medicines or food additives.

The present invention at least has the following beneficial effects:

According to the present invention, the anthocyanin is prepared by enzymolysis, ultrasonic treatment, multiple filtration and resin adsorption to improve the yield and purity; the microencapsulation method of anthocyanin is optimized by adopting improved process parameters (including the ratio of the core material to the wall material, parameter setting of spray drying and the like), to ensure the structural stability of anthocyanin; meanwhile, acetic acid is added to improve the structural stability of anthocyanin at high temperature and other conditions; and the microencapsulation method provided by the present invention has simple process and low operation cost.

Other advantages, objectives and characteristics of the present invention will be reflected by the following description, while some of them will be understood by those skilled in the art through the study and practice of the present invention.

DETAILED DESCRIPTION OF THE PRESENT INVENTION

Figure 1A:
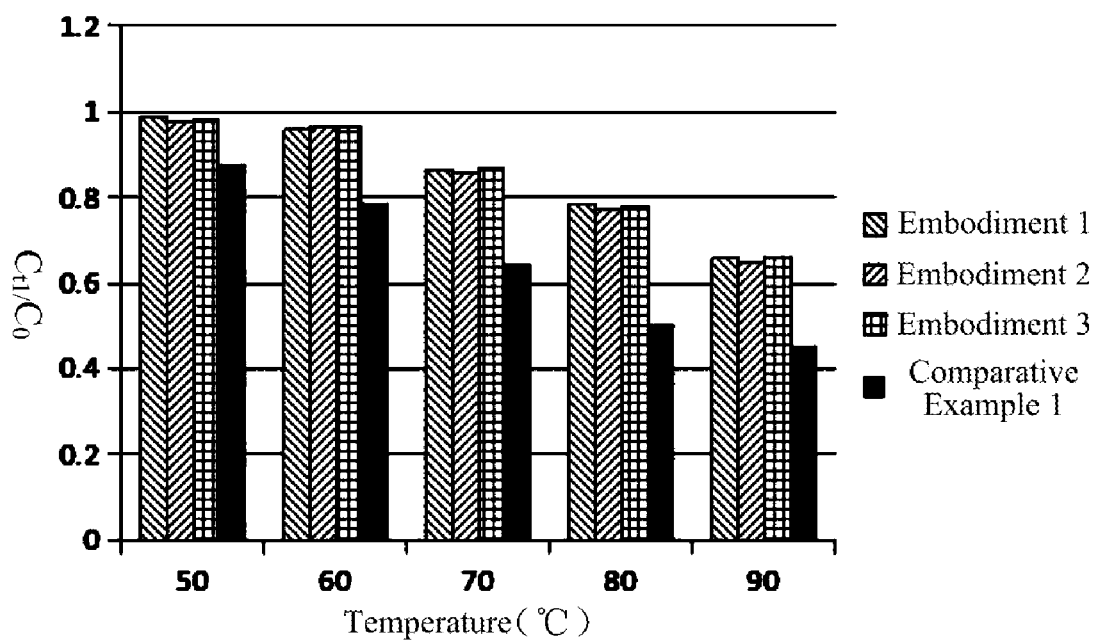
FIG. 1a shows influence of temperature on stability of anthocyanin.

The present invention will be further described in detail below in combination with embodiments, so that those skilled in the art can implement the present invention according to the text of the description.

It should be understood that terms such as "have", "contain" and "include" as used herein do not imply the presence or addition of one or more other elements or combinations thereof.

It should be noted that the experimental methods described in the following embodiments are conventional methods unless otherwise stated; and the reagents and materials can be obtained from commercial sources unless otherwise stated.

Embodiment 1

In the present embodiment, a microencapsulation method for improving the stability of anthocyanin includes the following steps:

S1, taking sodium alginate as a wall material, respectively preparing 2 g of sodium alginate, 1 g of calcium carbonate and 15 mL of water according to a weight ratio of the sodium alginate to the calcium carbonate to the water of 2:1:15 (the weight of 1 mL of water is regarded as 1 g, and the above weight unit and volume unit also fall within the protection scope of the present embodiment after being correspondingly expanded by the same multiple in the present embodiment), and then adding the sodium alginate and the calcium carbonate into the water to swell for 1 h to obtain a wall material gel system;

S2, dissolving 1 mg of freeze-dried anthocyanin in distilled water to prepare 1 mg/mL of anthocyanin solution, taking the anthocyanin as a core material, and fully and uniformly mixing the wall material gel system with 166.7 mL of anthocyanin solution for later use according to a weight ratio of the sodium alginate to the anthocyanin of 12:1 to obtain a water phase;

S3, mixing Span80 with vegetable oil (which is preferably soybean oil) at a volume ratio of 1:1 to obtain an oil phase, mixing the water phase with the oil phase at a volume ratio of 3:1, and magnetically stirring the mixture for emulsifying to obtain a W/O emulsion;

S4, adjusting the pH of the W/O emulsion to be acidic (the pH is preferably 3.5-4.5), mixing the W/O emulsion with a buffer solution at a volume ratio of 1:3, standing for 1 h, and separating the oil phase from the water phase to obtain a liquid anthocyanin microcapsule, wherein the step of adjusting the pH of the W/O emulsion to be acidic particularly includes: adding the vegetable oil containing an acidic solution into the W/O emulsion, in which the acidic solution is anhydrous acetic acid in the present embodiment, and a weight ratio of anhydrous acetic acid to calcium carbonate is 3:1; and the buffer solution is a phosphate buffer solution (0.1 mol/L, pH=7) containing NaCl with a mass concentration of 0.9%.

Further, for the convenience of storage and use, after step S4, the method further includes a step S5 of spray-drying the liquid anthocyanin microcapsule to obtain anthocyanin microcapsule powder under the conditions that the heater temperature is 100° C., the feed rate is 10 r/min, and the vacuum pressure is 0.02 MPa.

In the above microencapsulation method, sodium alginate is taken as the wall material to prepare the wet/solid anthocyanin microcapsule. Specifically, a sodium alginate solution, a water-insoluble calcium salt and an embedding substance are blended and dispersed into the oil phase to form the W/O emulsion; an acid is added to initiate the dissociation of $Ca^{2+}$ in the calcium salt, so that $Ca^{2+}$ reacts with sodium alginate in emulsion droplets to generate calcium alginate gel beads, thereby stabilizing the structure of the active substance by embedding the active substance and improving the stability of the structure. Meanwhile, the raw materials (such as sodium alginate, vegetable oil and salt) used in the above method are all food-grade nontoxic raw materials, and do not involve toxic organic reagents such as isopropyl-ketone, so that the method can be safely applied to the biology, food, medicine and other industries.

Further, in the step S2, the anthocyanin is prepared by the following processes:

S21, drying and crushing raw materials for extracting the anthocyanin, and sieving the obtained raw materials with a 200-300-mesh sieve to obtain raw material powder, wherein the raw materials are one or more of roots, stems, leaves and fruits of plants containing a red or purple pigment in the present embodiment;

S22, taking 1 g of raw material powder and 15 mL (the above weight unit and volume unit also fall within the protection scope of the present embodiment after being correspondingly expanded by the same multiple in the present embodiment) of extracting solution at a weight-volume ratio of 1:15 to be mixed uniformly; then adding a compound enzyme accounting for 0.02% by weight of the raw material powder to obtain an extraction system, performing ultrasonic extraction at 35° C. in the extraction system for 60 min, wherein the extracting solution includes 75% of 85% ethanol, 2% of 5% acetic acid, 12% of sucrose and 11% of choline chloride by weight, the ultrasonic power in the ultrasonic extraction is 200 W, the compound enzyme is composed of cellulase, pectinase and α-amylase, and the weight ratio of cellulase to pectinase to α-amylase is 1:1:1.5; and performing solid-liquid separation after the ultrasonic extraction to obtain a first filter residue and a first filtrate;

S23, adding 85% ethanol and 3% citric acid solution, which are 5 times the weight of the first filter residue and 0.2 time the weight of the first filter residue respectively, into the first filter residue, performing ultrasonic extraction at 35° C. for 45 min, and performing solid-liquid separation after the ultrasonic extraction to obtain a second filter residue and a second filtrate;

S24, combining the first filtrate with the second filtrate to obtain a crude extract, centrifuging the crude extract at 8000 rpm for removing precipitates to obtain a refined extract, and sequentially filtering the refined extract through a microfiltration membrane with an aperture of 2-5 μm, an ultrafiltration membrane with an aperture of 0.02-0.05 μm and a nanofiltration membrane with an aperture of 0.001-0.002 μm to obtain an extracted clear solution, wherein the filtration pressure is 0.2 MPa and the filtration temperature is 25° C. when the refined extract is filtered through the microfiltration membrane with the aperture of 2-5 μm and the ultrafiltration membrane with the aperture of 0.02-0.05 μm; and the filtration pressure is 1.5 MPa and the filtration temperature is 25° C. when the refined extract is filtered through the nanofiltration membrane with the aperture of 0.001-0.002 μm;

S25, adding 85% ethanol, which is double the volume of the extracted clear solution, into the extracted clear solution, centrifuging at 12000 rpm for 15 min, making the supernatant obtained after discarding precipitates pass through a column filled with XAD-7HP macroporous adsorption resin, wherein a volume ratio of the supernatant to the column is 3:1, eluting the macroporous adsorption resin with 5% ethanol to remove impurities after the macroporous adsorption resin forms a saturated uniform color band, then desorbing the pigment adsorbed by the macroporous adsorption resin with 1 column volume of 70% acidic ethanol until the macroporous adsorption resin is colorless, and collecting eluent;

S26, concentrating the eluent by a high-pressure reverse osmosis membrane after passing through the ultrafiltration membrane with the aperture of 0.02-0.05 μm, to obtain an intercepted concentrated solution with a solid content of 15%, wherein the interception molecular weight of the high-pressure reverse osmosis membrane is 200 Da, the concentration temperature is 25° C., and the concentration pressure is 3.0 MPa during concentration by the high-pressure reverse osmosis membrane;

S27, concentrating the intercepted concentrated solution under vacuum and reduced pressure at 35° C. until ethanol is completely removed, to obtain a concentrated solution with a Baume degree of 3°; and S28, adding 10% acetic acid, which is 4% by volume of the concentrated solution, into the concentrated solution, heating at 30° C. for 30 min, rapidly freezing at −70° C., and then freeze-drying to obtain the anthocyanin.

Embodiment 2

In the present embodiment, a microencapsulation method for improving the stability of anthocyanin includes the following steps:

S1, taking sodium alginate as a wall material, respectively preparing 3 g of sodium alginate, 1 g of calcium carbonate and 20 mL of water according to a weight ratio of the sodium alginate to the calcium carbonate to the water of 3:1:20, and then adding the sodium alginate and the calcium carbonate into the water to swell for 2 h to obtain a wall material gel system;

S2, dissolving 1 mg of freeze-dried anthocyanin in distilled water to prepare 1 mg/mL of anthocyanin solution, taking the anthocyanin as a core material, and fully and uniformly mixing the wall material gel system with 200 mL of anthocyanin solution for later use according to a weight ratio of the sodium alginate to the anthocyanin of 15:1 to obtain a water phase;

S3, mixing Span80 with vegetable oil (which is preferably soybean oil) at a volume ratio of 2:1 to obtain an oil phase, mixing the water phase with the oil phase at a volume ratio of 5:1, and magnetically stirring the mixture for emulsifying to obtain a W/O emulsion;

S4, adjusting the pH of the W/O emulsion to be acidic (the pH is preferably 3.0), mixing the W/O emulsion with a buffer solution at a volume ratio of 1:5, standing for 2 h, and separating the oil phase from the water phase to obtain a liquid anthocyanin microcapsule;

S5, spray-drying the liquid anthocyanin microcapsule to obtain anthocyanin microcapsule powder under the conditions that the heater temperature is 130° C., the feed rate is 15 r/min, and the vacuum pressure is 0.05 MPa.

Further, in the step S2, the anthocyanin is prepared by the following processes:

S21, drying and crushing raw materials for extracting the anthocyanin, and sieving the obtained raw materials with a 200-300-mesh sieve to obtain raw material powder;

S22, mixing the raw material powder with an extracting solution at a weight-volume ratio of 1:20 uniformly; then adding a compound enzyme accounting for 0.03% by weight of the raw material powder to obtain an extraction system; performing ultrasonic extraction at 35° C. in the extraction system for 60 min, wherein the extracting solution includes 74% of 85% ethanol, 4% of 5% acetic acid, 10% of sucrose and 12% of choline chloride by weight, the ultrasonic power in the ultrasonic extraction is 300 W, the compound enzyme is composed of cellulase, pectinase and α-amylase, and the weight ratio of cellulase to pectinase to α-amylase is 1:1:1.5; and performing solid-liquid separation after the ultrasonic extraction to obtain a first filter residue and a first filtrate;

S23, adding 85% ethanol and 3% citric acid solution, which are 7 times the weight of the first filter residue and 0.3 time the weight of the first filter residue respectively, into the first filter residue, performing ultrasonic extraction at 45° C. for 60 min, and performing solid-liquid separation after the ultrasonic extraction to obtain a second filter residue and a second filtrate;

S24, combining the first filtrate with the second filtrate to obtain a crude extract, centrifuging the crude extract at 10000 rpm for removing precipitates to obtain a refined extract, and sequentially filtering the refined extract through a microfiltration membrane with an aperture of 2-5 μm, an ultrafiltration membrane with an aperture of 0.02-0.05 μm and a nanofiltration membrane with an aperture of 0.001-0.002 μm to obtain an extracted clear solution, wherein the filtration pressure is 0.4 MPa and the filtration temperature is 35° C. when the refined extract is filtered through the microfiltration membrane with the aperture of 2-5 μm and the ultrafiltration membrane with the aperture of 0.02-0.05 μm; and the filtration pressure is 2.0 MPa and the filtration temperature is 35° C. when the refined extract is filtered through the nanofiltration membrane with the aperture of 0.001-0.002 μm;

S25, adding 85% ethanol, which is twice the volume of the extracted clear solution, into the extracted clear solution, centrifuging at 12000 rpm for 15 min, making the supernatant obtained after discarding precipitates pass through a column filled with XAD-7HP macroporous adsorption resin, wherein a volume ratio of the supernatant to the column is 3:1, eluting the macroporous adsorption resin with 5% ethanol to remove impurities after the macroporous adsorption resin forms a saturated uniform color band, then desorbing the pigment adsorbed by the macroporous adsorption resin with 2 column volumes of 70% acidic ethanol until the macroporous adsorption resin is colorless, and collecting eluent;

S26, concentrating the eluent by a high-pressure reverse osmosis membrane after passing through the ultrafiltration membrane with the aperture of 0.02-0.05 μm, to obtain an intercepted concentrated solution with a solid content of 25%, wherein the interception molecular weight of the high-pressure reverse osmosis membrane is 200 Da, the concentration temperature is 35° C., and the concentration pressure is 4.5 MPa during concentration by the high-pressure reverse osmosis membrane;

S27, concentrating the intercepted concentrated solution under vacuum and reduced pressure at 55° C. until ethanol is completely removed, to obtain a concentrated solution with a Baume degree of 5°; and S28, adding 10% acetic acid, which is 5% by volume of the concentrated solution, into the concentrated solution, heating at 40° C. for 30 min, rapidly freezing at −70° C., and then freeze-drying to obtain the anthocyanin.

Other technical characteristics of the present embodiment are the same as those in embodiment 1 and will not be repeated here.

Embodiment 3

A microencapsulation method for improving the stability of anthocyanin includes the following steps:

S1, taking sodium alginate as a wall material, respectively preparing 4 g of sodium alginate, 1 g of calcium carbonate and 25 mL of water according to a weight ratio of sodium alginate to calcium carbonate to water of 4:1:25, and then adding sodium alginate and calcium carbonate into the water to swell for 2 h to obtain a wall material gel system;

S2, dissolving 1 mg of freeze-dried anthocyanin in distilled water to prepare 1 mg/mL of anthocyanin solution, taking the anthocyanin as a core material, and fully and uniformly mixing the wall material gel system with 200 mL of anthocyanin solution for later use according to a weight ratio of the sodium alginate to the anthocyanin of 20:1 to obtain a water phase;

S3, mixing Span80 with vegetable oil (which is preferably soybean oil) at a volume ratio of 1.5:1 to obtain an oil phase, mixing the water phase with the oil phase at a volume ratio of 4:1, and magnetically stirring the mixture for emulsifying to obtain a W/O emulsion;

S4, adjusting the pH of the W/O emulsion to be acidic (the pH is preferably 4.0), mixing the W/O emulsion with a buffer solution at a volume ratio of 1:4, standing for 1.5 h, and separating the oil phase from the water phase to obtain a liquid anthocyanin microcapsule;

S5, spray-drying the liquid anthocyanin microcapsule to obtain anthocyanin microcapsule powder under the conditions that the heater temperature is 120° C., the feed rate is 12 r/min, and the vacuum pressure is 0.03 MPa.

Further, in the step S2, the anthocyanin is prepared by the following processes:

S21, drying and crushing raw materials for extracting the anthocyanin, and sieving the obtained raw materials with a 200-300-mesh sieve to obtain raw material powder;

S22, mixing the raw material powder with an extracting solution at a weight-volume ratio of 1:18 uniformly; then adding a compound enzyme accounting for 0.025% by weight of the raw material powder to obtain an extraction system; performing ultrasonic extraction at 40° C. in the extraction system for 75 min, wherein the extracting solution includes 73% of 85% ethanol, 3% of 5% acetic acid, 12% of sucrose and 12% of choline chloride; the ultrasonic power in the ultrasonic extraction is 400 W; the compound enzyme is composed of cellulase, pectinase and α-amylase and the weight ratio of cellulase to pectinase to α-amylase is 1:1:1.5; and performing solid-liquid separation after the ultrasonic extraction to obtain a first filter residue and a first filtrate;

S23, adding 85% ethanol and 3% citric acid solution, which are 8 times the weight of the first filter residue and 0.25 time the weight of the first filter residue respectively, into the first filter residue, performing ultrasonic extraction at 40° C. for 50 min, and performing solid-liquid separation after the ultrasonic extraction to obtain a second filter residue and a second filtrate;

S24, combining the first filtrate with the second filtrate to obtain a crude extract, centrifuging the crude extract at 11000 rpm for removing precipitates to obtain a refined extract, and sequentially filtering the refined extract through a microfiltration membrane with an aperture of 2-5 μm, an ultrafiltration membrane with an aperture of 0.02-0.05 μm and a nanofiltration membrane with an aperture of 0.001-0.002 μm to obtain an extracted clear solution, wherein the filtration pressure is 0.3 MPa and the filtration temperature is 30° C. when the refined extract is filtered through the microfiltration membrane with the aperture of 2-5 μm and the ultrafiltration membrane with the aperture of 0.02-0.05 μm; and the filtration pressure is 1.8 MPa and the filtration temperature is 30° C. when the refined extract is filtered through the nanofiltration membrane with the aperture of 0.001-0.002 μm;

S25, adding 85% ethanol, which is 1.5 times the volume of the extracted clear solution, into the extracted clear solution, centrifuging at 12000 rpm for 15 min, making the supernatant obtained after discarding precipitates pass through a column filled with XAD-7HP macroporous adsorption resin, wherein a volume ratio of the supernatant to the column is 3:1, eluting the macroporous adsorption resin with 5% ethanol to remove impurities after the macroporous adsorption resin forms a saturated uniform color band, then desorbing the pigment adsorbed by the macroporous adsorption resin with 1.5 column volumes of 70% acidic ethanol until the macroporous adsorption resin is colorless, and collecting eluent;

S26, concentrating the eluent by a high-pressure reverse osmosis membrane after passing through the ultrafiltration membrane with the aperture of 0.02-0.05 μm, to obtain an intercepted concentrated solution with a solid content of 20%, wherein the interception molecular weight of the high-pressure reverse osmosis membrane is 200 Da, the concentration temperature is 30° C., and the concentration pressure is 4.0 MPa during concentration by the high-pressure reverse osmosis membrane;

S27, concentrating the intercepted concentrated solution under vacuum and reduced pressure at 45° C. until ethanol is completely removed, to obtain a concentrated solution with a Baume degree of 4°; and S28, adding 10% acetic acid, which is 4.5% by volume of the concentrated solution, into the concentrated solution, heating at 35° C. for 30 min, rapidly freezing at −70° C., and then freeze-drying to obtain the anthocyanin.

Other technical characteristics of the present embodiment are the same as those in embodiment 1 and will not be repeated here.

<Detection on Yield and Purity of Anthocyanin>

Figure 1B:
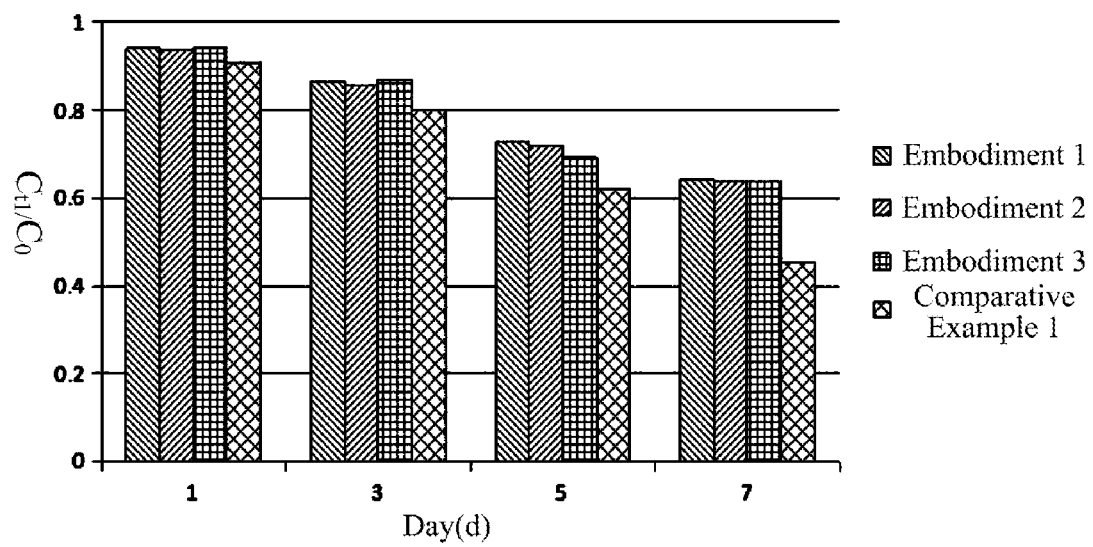
FIG. 1b shows influence of light on stability of anthocyanin.
Figure 1C:
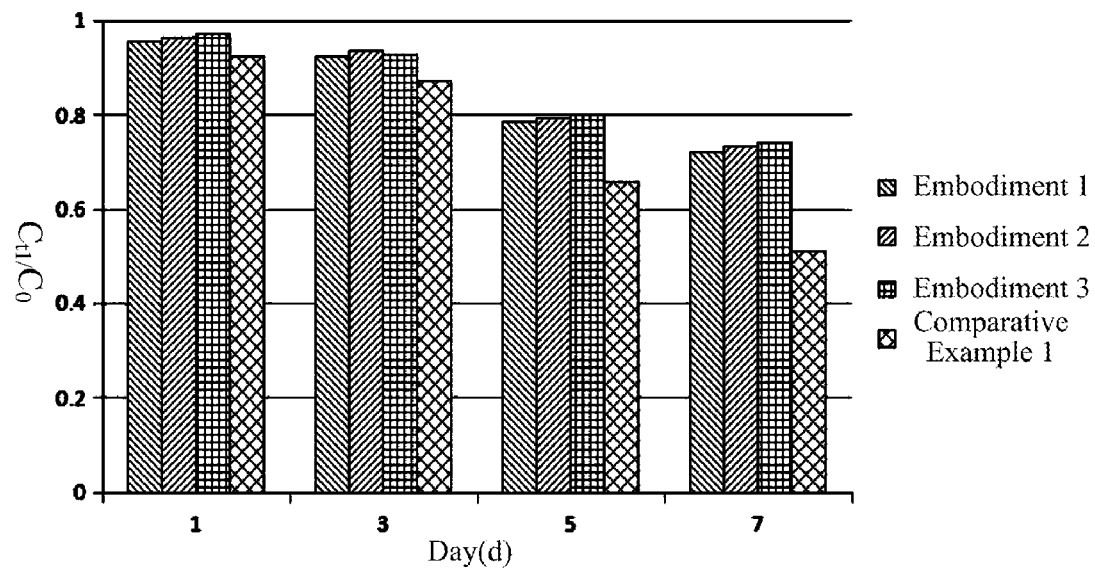
FIG. 1c shows influence of dark on stability of anthocyanin.

Grape skin was crushed, and then was heated and refluxed with ethanol for 2-3 times. The extracting solution was filtered for recovering ethanol to obtain a primary extract. The pH value of the primary extract was adjusted to 2.5-3.0. The extract was centrifugally separated to collect precipitates. The precipitates were washed with water to be neutral to obtain a crude anthocyanin extract. The obtained crude anthocyanin extract was adsorbed with macroporous adsorption resin, and then eluted with ethanol to collect eluent. The eluent was spray-dried to obtain the anthocyanin as a comparative example 1. The purity, the yield, the content, the superoxide anion ($O_2\cdot$) scavenging capacity and the hydroxyl radical ($OH\cdot$) scavenging capacity of the anthocyanin prepared by the preparation methods in embodiments 1-3 of the present invention were detected to obtain results as shown in Table 1.1. In addition, FIGS. 1a-1c show influences of temperature and light on the stability of the anthocyanin prepared in the present invention and that prepared in the Comparative Example 1, wherein the anthocyanin preservation rate (%)=$C_{t1}/C_0$; $C_0$ is an initial absorbance value of anthocyanin solution; and $C_{t1}$ is an absorbance value of the solution treated by light and temperature.

TABLE 1.1

Detection on Purity, Yield, Content, $O_2\bullet$- Scavenging Rate and $OH\bullet$ Scavenging Rate of Anthocyanin

| Index | Embodiment 1 | Embodiment 2 | Embodiment 3 | Comparative Example 1 |
|---|---|---|---|---|
| Purity (%) | 93.42 | 94.24 | 93.12 | 86.78 |
| Yield (%) | 12.24 | 11.79 | 12.59 | 8.64 |
| $O_2\bullet$- scavenging rate (%) | 88.57 | 91.61 | 87.64 | 75.62 |
| $OH\bullet$ scavenging rate (%) | 91.25 | 92.16 | 90.14 | 78.23 |
| Content (g/mg) | 123.95 | 121.56 | 125.63 | 102.35 |

Table 1 shows that the purity and the yield of anthocyanin prepared in embodiments 1-3 of the present invention are 93.59% and 12.2% on average, which are respectively increased by 7.8% and 41% compared with those prepared in comparative example 1. Further, the superoxide anion ($O_2\cdot$) scavenging capacity and the hydroxyl radical ($OH\cdot$) scavenging capacity of anthocyanin prepared in the present invention are significantly increased by 18% and 16.5% respectively; and the content of anthocyanin prepared in embodiments 1-3 is increased by 21% compared with that prepared in comparative example 1. Meanwhile, FIG. 1a shows that the preservation rates of anthocyanin in embodiments 1-3 and comparative example 1 are decreased with the rise of temperature, but the decreasing speeds of the preservation rates of anthocyanin in embodiments 1-3 are apparently less than that in comparative example 1, and the preservation rates of anthocyanin prepared in the present invention are all significantly greater than that in comparative example 1 after treatment at the same temperature. FIG. 1b shows that light will influence the stability of anthocyanin in embodiments 1-3 and comparative example 1, to decrease the preservation rates; but the decreasing speeds of the preservation rates of anthocyanin in embodiments 1-3 are apparently less than that in comparative example 1 in light; and the preservation rates of anthocyanin in embodiments 1-3 are all significantly greater than that in comparative example 1 after treatment in the same light conditions. In addition, FIG. 1c shows that the preservation rates of anthocyanin in embodiments 1-3 and comparative example 1 after the same period of treatment in dark are all greater than those in light, which indicates that the dark conditions are beneficial for the preservation of anthocyanin.

The reasons are that, in the present invention, firstly, cell walls were fully hydrolyzed by the compound enzyme through ultrasonic extraction to fully release the contained anthocyanin, thereby increasing the yield; the extracting solution with a special ratio was adopted; the anthocyanin was further extracted by ethanol in the extracting solution; meanwhile, acetic acid, sucrose and choline chloride were taken as group donors, to enhance the structural stability of anthocyanin through intermolecular or intramolecular copigmentation; at the same time, the anthocyanin was purified by multiple filtration membranes and macroporous adsorption resin to improve the purity; and finally, acetic acid was added as hydrogen bond donor to further stabilize the structure of anthocyanin.

Embodiment 4

The present embodiment provides an anthocyanin microcapsule product prepared by the microencapsulation method according to any one of embodiments 1-3.

Parameters for preparing anthocyanin microcapsule powder (hereinafter referred to as "anthocyanin microcapsule powder") according to the present invention will be optimized below by the procedures as follows.

1. Major factors that influence the preparation of anthocyanin microcapsules were screened by Plackett-Burman design.

The concentration of sodium alginate (NaALG), the mass ratio of $CaCO_3$ to NaALG, the ratio of wall materials to core materials (i.e., the weight ratio of the sodium alginate to the anthocyanin), the volume ratio of water phase to oil phase, the concentration of Span80, the emulsification rate, the ratio of acid to calcium (i.e., the weight ratio of acidic solution to calcium carbonate), the acidification time, the mass concentration of NaCl and the like were selected as factor levels according to the preparation technology of microcapsules and are screened to obtain the major factors. A table for factors and levels of Plackett-Burman design is shown in Table 1.

TABLE 1

Table for Factors and Levels of Plackett-Burman Design

| Factor | Unit | Lower level (−1) | Upper level (1) |
|---|---|---|---|
| Concentration of NaALG ($X_1$) | g/L | 15 | 20 |
| Mass ratio of $CaCO_3$ to NaALG ($X_2$) | Ratio | 1:3 | 1:5 |
| Ratio of wall materials to core materials ($X_3$) | Ratio | 1:15 | 1:20 |
| Volume ratio of water phase to oil phase ($X_4$) | Ratio | 1:3 | 1:06 |
| Concentration of Span80 ($X_5$) | Percentage | 1% | 1.5% |
| Emulsification rate ($X_6$) | r/min | 400 | 600 |
| Ratio of acid to calcium($X_8$) | Ratio | 3:1 | 5:1 |
| Acidification time ($X_{10}$) | min | 40 | 60 |
| Concentration of NaCl ($X_{11}$) | Percentage | 0.9 | 1.5 |

2. The maximum response region of a response surface was approached according to the major factors screened by Plackett-Burman design and positive and negative trends of the major factors.

3. The maximum value of a steepest ascent experiment was selected as the central point, of which the upper level and the lower level were taken respectively; four factors with the greatest influence on the encapsulation rate and the average particle size were selected as independent variables by taking the encapsulation rate and the average particle size of anthocyanin microcapsules as response values according to Box-Behnken central design principles; and the response surface with four factors and three levels was designed by software Design Expert, to optimize and verify the preparation conditions in an endogenous emulsification method for preparing anthocyanin microcapsules.

The significant factors influencing the encapsulation rate were screened by the Plackett-Burman design. 9 factors and 12 groups of experiments were available according to the experimental design in Table 2. The encapsulation rate was taken as an investigation index to obtain experimental results in Table 3.

The order of factors obtained from the regression equation is as follows: $X_{11}$ (the concentration of NaCl)>$X_8$ (the ratio of acid to calcium)>$X_2$ (the mass ratio of $CaCO_3$ to NaALG) >$X_3$ (the ratio of wall materials to core materials)>$X_6$ (the emulsification rate)>$X_5$ (the concentration of Span80)>$X_1$ (the concentration of NaALG)>$X_4$ (the volume ratio of oil phase to water phase)>$X_{10}$ (the acidification time).

Investigation results of the regression equation are obtained from the experimental results in Table 2, as shown in Table 3. Table 3 shows that the whole model is significant; the major factors screened by Plackett-Burman design include the mass ratio of $CaCO_3$ to NaALG, the ratio of wall materials to core materials, the acidification ratio and the mass concentration of NaCl, which significantly influence the encapsulation rate and are all negatively correlated with the investigation indexes; and the other factors are also negatively correlated with the investigation indexes; therefore, the lower level is selected. The corresponding steepest ascent experiment was designed according to the steepness negatively correlated with the selected major factors, so that a response surface method can be better used to optimize the encapsulation rate and the particle size.

TABLE 2

Results of Plackett-Burman Experiment Design

| N | $x_1$ | $x_2$ | $x_3$ | $x_4$ | $x_5$ | $x_6$ | $x_7$ | $x_8$ | $x_9$ | $x_{10}$ | $x_{11}$ | Y The encapsulation rate (%) |
|---|---|---|---|---|---|---|---|---|---|---|---|---|
| 1 | 20 | 3 | 20 | 3 | 1.0 | 400 | 1 | 5 | 1 | 40 | 1.5 | 62.9 ± 0.6 |
| 2 | 20 | 5 | 15 | 6 | 1.0 | 600 | −1 | 5 | 1 | 60 | 0.9 | 67.6 ± 0.2 |
| 3 | 15 | 5 | 20 | 3 | 1,5 | 400 | −1 | 3 | 1 | 60 | 1.5 | 63.7 ± 0.4 |
| 4 | 20 | 3 | 20 | 6 | 1.0 | 600 | −1 | 3 | −1 | 60 | 1.5 | 64.4 ± 0.5 |
| 5 | 20 | 5 | 15 | 6 | 1.5 | 400 | 1 | 3 | −1 | 40 | 1.5 | 60.1 ± 0.7 |
| 6 | 20 | 5 | 20 | 3 | 1.5 | 600 | −1 | 5 | −1 | 40 | 0.9 | 59.5 ± 0.5 |
| 7 | 15 | 5 | 20 | 6 | 1.0 | 600 | 1 | 3 | 1 | 40 | 0.9 | 50.0 ± 0.9 |
| 8 | 15 | 3 | 20 | 6 | 1.5 | 400 | 1 | 5 | −1 | 60 | 0.9 | 52.3 ± 0.3 |
| 9 | 15 | 3 | 15 | 6 | 1.5 | 600 | −1 | 5 | 1 | 40 | 1.5 | 53.6 ± 0.7 |
| 10 | 20 | 3 | 15 | 3 | 1.5 | 600 | 1 | 3 | 1 | 60 | 0.9 | 65.9 ± 0.6 |
| 11 | 15 | 5 | 15 | 3 | 1.0 | 600 | 1 | 5 | −1 | 60 | 1.5 | 77.1 ± 0.2 |
| 12 | 15 | 3 | 15 | 3 | 1.0 | 400 | −1 | 3 | −1 | 40 | 0.9 | 61.3 ± 0.4 |

TABLE 3

Investigation Results of Regression Equation

| | DF | Sum of Square | Mean Square | F | p | Significance |
|---|---|---|---|---|---|---|
| Model | 4 | 571.64 | 66.26 | 32.45 | 0.0302 < 0.05 | * |
| Mass ratio of $CaCO_3$ to NaALG | 1 | 137.36 | 137.36 | 67.28 | 0.0145 < 0.05 | |
| Ratio of wall materials to core materials | 1 | 46.41 | 46.41 | 22.73 | 0.0413 < 0.05 | * |
| Ratio of acid to calcium | 1 | 177.87 | 177.87 | 87.12 | 0.0113 < 0.05 | * |
| Concentration of NaCl | 1 | 210 | 177.87 | 102.86 | 0.0096 < 0.05 | * |
| Residual | 7 | 28.79 | 2.04 | | | |
| Cor Total | 11 | 600.43 | | | | |

Note a:

* represents that the influence is significant, and P < 0.05.

The conclusion obtained from the experiment design in Table 2 and the Plackett-Burman experiment indicates that the steepest ascent experiment is designed according to the descending order of factors due to the major factors selected are negatively correlated with the encapsulation rate. The encapsulation rate was taken as the investigation index, and the average particle size of different experiment designs was compared, to obtain results as shown in Table 4.

TABLE 4

Results of Steepest Ascent Experiment

| Run | Mass ratio of $CaCO_3$ to NaALG | Ratio of wall materials to core materials | Ratio of acid to calcium | Concentration of NaCl (%) | Encapsulation rate(%) | Average particle size (μm) |
|---|---|---|---|---|---|---|
| 1 | 1:3   | 1:15 | 3   | 0.9 | 67.9 ± 0.5 | 156 ± 3 |
| 2 | 1:2.5 | 1:14 | 2.9 | 0.8 | 65.2 ± 0.2 | 192 ± 5 |
| 3 | 1:2   | 1:13 | 2.8 | 0.7 | 62.0 ± 0.7 | 217 ± 2 |
| 4 | 1:1.5 | 1:12 | 2.7 | 0.6 | 60.5 ± 0.4 | 247 ± 3 |
| 5 | 1:1   | 1:11 | 2.6 | 0.5 | 56.2 ± 0.6 | 283 ± 6 |

The central point of the response surface was determined as follows according to the steepest ascent experiment: the mass ratio of $CaCO_3$ to NaALG was 1:3, the ratio of wall materials to core materials was 1:15, the ratio of acid to calcium was 3, and the mass concentration of NaCl was 0.9%. Under these conditions, the encapsulation rate was determined to be 67.9%.

On the basis of the Plackett-Burman experiment and steepest ascent experiment designs, the response surface experiment was designed and analyzed to determine the optimal process conditions for preparing anthocyanin microcapsules. Experiment factors and levels are shown in Table 5; and solutions and results for experiment designs are shown in Table 6.

TABLE 5

Table for Experiment Factors and Levels of Response Surface

| Factor | Code | Level −1 | Level 0 | Level 1 |
|---|---|---|---|---|
| Mass ratio of NaALG to $CaCO_3$ | $X_1$ | 2 | 3 | 4 |
| Ratio of wall materials to core materials | $X_2$ | 14 | 15 | 16 |
| Ratio of acid to calcium | $X_3$ | 2 | 3 | 4 |
| Concentration of NaCl(%) | $X_4$ | 0.8 | 0.9 | 1 |

TABLE 6

Experiment Design (Box-Behnken design) of Response Surface and Results

| Std | Run | Mass ratio of NaALG to $CaCO_3$ | Ratio of wall materials to core materials | Ratio of acid to calcium | Concentration of NaCl(%) | $Y_1$ The encapsulation rate (%) | $Y_2$ The average particle size (μm) |
|---|---|---|---|---|---|---|---|
| 24 | 1  | 3 | 16 | 3 | 1   | 60.42 ± 0.21 | 149 ± 2 |
| 13 | 2  | 3 | 14 | 2 | 0.9 | 49.69 ± 0.33 | 200 ± 6 |
| 6  | 3  | 3 | 15 | 4 | 0.8 | 60.84 ± 0.29 | 194 ± 4 |
| 28 | 4  | 3 | 15 | 3 | 0.9 | 75.85 ± 0.26 | 125 ± 3 |
| 2  | 5  | 4 | 14 | 3 | 0.9 | 56.39 ± 0.31 | 194 ± 5 |
| 21 | 6  | 3 | 14 | 3 | 0.8 | 69.97 ± 0.22 | 135 ± 7 |
| 14 | 7  | 3 | 16 | 2 | 0.9 | 61.96 ± 0.35 | 184 ± 3 |
| 18 | 8  | 4 | 15 | 2 | 0.9 | 57.41 ± 0.19 | 158 ± 6 |
| 12 | 9  | 4 | 15 | 3 | 1   | 71.62 ± 0.34 | 197 ± 5 |
| 26 | 10 | 3 | 15 | 3 | 0.9 | 75.43 ± 0.27 | 119 ± 2 |
| 25 | 11 | 3 | 15 | 3 | 0.9 | 76.12 ± 0.39 | 121 ± 8 |
| 20 | 12 | 4 | 15 | 4 | 0.9 | 58.03 ± 0.30 | 145 ± 4 |
| 5  | 13 | 3 | 15 | 2 | 0.8 | 35.35 ± 0.33 | 127 ± 6 |
| 29 | 14 | 3 | 15 | 3 | 0.9 | 72.78 ± 0.20 | 120 ± 3 |
| 16 | 15 | 3 | 16 | 4 | 0.9 | 58.92 ± 0.27 | 130 ± 8 |
| 19 | 16 | 2 | 15 | 4 | 0.9 | 53.7 ± 0.36  | 167 ± 2 |
| 7  | 17 | 3 | 15 | 2 | 1   | 56.56 ± 0.18 | 172 ± 4 |
| 22 | 18 | 3 | 16 | 3 | 0.8 | 59.45 ± 0.41 | 164 ± 3 |
| 27 | 19 | 3 | 15 | 3 | 0.9 | 70.08 ± 0.22 | 114 ± 8 |
| 1  | 20 | 2 | 14 | 3 | 0.9 | 64.27 ± 0.25 | 182 ± 7 |
| 23 | 21 | 3 | 14 | 3 | 1   | 58.8 ± 0.24  | 230 ± 4 |
| 9  | 22 | 2 | 15 | 3 | 0.8 | 59.05 ± 0.16 | 131 ± 2 |
| 4  | 23 | 4 | 16 | 3 | 0.9 | 60.96 ± 0.19 | 211 ± 3 |
| 10 | 24 | 4 | 15 | 3 | 0.8 | 54.38 ± 0.29 | 163 ± 4 |
| 11 | 25 | 2 | 15 | 3 | 1   | 50.26 ± 0.37 | 193 ± 5 |
| 17 | 26 | 2 | 15 | 2 | 0.9 | 52.4 ± 0.33  | 163 ± 2 |
| 3  | 27 | 2 | 16 | 3 | 0.9 | 59.32 ± 0.31 | 169 ± 3 |
| 8  | 28 | 3 | 15 | 4 | 1   | 63.96 ± 0.30 | 156 ± 6 |
| 15 | 29 | 3 | 14 | 4 | 0.9 | 61.41 ± 0.25 | 138 ± 2 |

The software Design expert was used for fitting the data in Table 6 by quadratic multiple regression, to obtain a quadratic multiple regression model of encapsulation rate to $X_1$, $X_2$, $X_3$ and $X_4$ as follows:

$$Y_1 = -1459.952 - 44.51483X_1 + 125.48667X_2 + 168.45017X_3 + 867.24667X_4 + 2.38X_1X_2 - 0.17X_1X_3 + 65.075X_1X_4 - 3.69X_2X_3 + 30.35X_2X_4 - 45.225X_3X_4 - 7.93225X_1^2 - 4.961X_2^2 - 11.37725X_3^2 - 757.35X_4^2 \quad (1).$$

A quadratic multiple regression equation of the average particle size to $X_1$, $X_2$, $X_3$ and $X_4$ is:

$$Y_2 = 5431.2 - 213.85X_1 - 747.5X_2 + 85.23X_3 + 1034.5X_4 + 7.5X_1X_2 - 4.25X_1X_3 - 70X_1X_4 + 2X_2X_3 - 275X_2X_4 - 207.5X_3X_4 + 30.39X_1^2 + 32.02X_2^2 + 13.02X_3^2 + 2264.17X_4^2 \quad (2).$$

The results of variance analysis of the above quadratic multiple regression model are shown in Tables 7-8.

TABLE 7

| | $Y_1$, Results of Variance Analysis for Encapsulation Rate | | | | | |
|---|---|---|---|---|---|---|
| Sources of variation | Sum of squares | Degree of freedom | Mean square | F value | P value | Significance |
| Model | 1813.63 | 14 | 129.54 | 4.2 | 0.0056 | ** |
| $X_1$ | 32.64 | 1 | 32.64 | 1.06 | 0.3211 | N |
| $X_2$ | 0.021 | 1 | 0.021 | $6.755 \times 10^{-4}$ | 0.9796 | N |
| $X_3$ | 157.62 | 1 | 157.62 | 5.11 | 0.0402 | * |
| $X_4$ | 42.49 | 1 | 42.49 | 1.38 | 0.2601 | N |
| $X_1X_2$ | 22.66 | 1 | 22.66 | 0.73 | 0.4058 | N |
| $X_1X_3$ | 0.12 | 1 | 0.12 | $3.748 \times 10^{-3}$ | 0.952 | N |
| $X_1X_4$ | 169.39 | 1 | 169.39 | 5.49 | 0.0344 | ** |
| $X_2X_3$ | 54.46 | 1 | 54.46 | 1.77 | 0.2051 | N |
| $X_2X_4$ | 36.84 | 1 | 36.84 | 1.19 | 0.2928 | N |
| $X_3X_4$ | 81.81 | 1 | 81.81 | 2.65 | 0.1257 | N |
| $X_1^2$ | 408.13 | 1 | 408.13 | 13.23 | 0.0027 | ** |
| $X_2^2$ | 159.64 | 1 | 159.64 | 5.18 | 0.0392 | * |
| $X_3^2$ | 839.62 | 1 | 839.62 | 27.22 | 0.0001 | ** |
| $X_4^2$ | 372.05 | 1 | 372.05 | 12.06 | 0.0037 | ** |
| Residual | 431.78 | 14 | 30.84 | | | |
| Lack of fit | 404.98 | 10 | 40.5 | 6.04 | 0.0489 | * |
| Pure error | 26.8 | 4 | 6.7 | | | |
| Total deviation | 2245.41 | 28 | | | | |

Note a:
** represents that the influence is extremely significant, and P < 0.01;
Note b:
* represents that the influence is significant, and P < 0.05;
Note c:
N represents that the influence is not significant, and P > 0.05. (The same below)

TABLE 8

| | $Y_2$, Results of Variance Analysis for Mean Particle Size | | | | | |
|---|---|---|---|---|---|---|
| Sources of variation | Sum of squares | Degree of freedom | Mean square | F value | P value | Significance |
| Model | 21027.28 | 14 | 1501.95 | 3.16 | 0.02 | * |
| $X_1$ | 330.75 | 1 | 330.75 | 0.70 | 0.42 | N |
| $X_2$ | 432.00 | 1 | 432.00 | 0.91 | 0.36 | N |
| $X_3$ | 456.33 | 1 | 456.33 | 0.96 | 0.34 | N |
| $X_4$ | 2790.75 | 1 | 2790.75 | 5.87 | 0.03 | ** |
| $X_1X_2$ | 225.00 | 1 | 225.00 | 0.47 | 0.50 | N |
| $X_1X_3$ | 72.25 | 1 | 72.25 | 0.15 | 0.70 | N |
| $X_1X_4$ | 196.00 | 1 | 196.00 | 0.41 | 0.53 | N |
| $X_2X_3$ | 16.00 | 1 | 16.00 | 0.03 | 0.86 | N |
| $X_2X_4$ | 3025.00 | 1 | 3025.00 | 6.36 | 0.02 | * |
| $X_3X_4$ | 1722.25 | 1 | 1722.25 | 3.62 | 0.08 | * |
| $X_1^2$ | 5991.27 | 1 | 5991.27 | 12.60 | 0.00 | ** |
| $X_2^2$ | 6649.08 | 1 | 6649.08 | 13.99 | 0.00 | ** |
| $X_3^2$ | 1099.03 | 1 | 1099.03 | 2.31 | 0.15 | N |
| $X_4^2$ | 3325.27 | 1 | 3325.27 | 6.99 | 0.02 | * |
| Residual | 6655.55 | 14 | 475.40 | | | |
| Lack of fit | 6592.75 | 10 | 659.27 | 41.99 | 0.00 | ** |
| Pure error | 62.80 | 4 | 15.70 | | | |
| Total deviation | 27682.83 | 28 | | | | |

The regression equation $Y_1$ was tested to obtain P<0.01, which indicates that the regression equation is extremely significant, has a good fitting degree, and has practical application and guiding significance. The regression equation coefficients were tested for significance (Table 7), which indicates that the quadratic term $X_1^2$ of the mass ratio of NaALG to $CaCO_3$, the quadratic term $X_3^2$ of the ratio of acid to calcium and the quadratic term $X_4^2$ of the concentration of NaCl have significant influence on the encapsulation rate of anthocyanin; the ratio $X_3$ of wall materials to core materials, the interaction $X_1X_4$ between the mass ratio of NaALG to $CaCO_3$ and the concentration of NaCl, and the quadratic term $X_2^2$ of the ratio of wall materials to core materials have significant influence on the encapsulation rate of anthocyanin; and other variables have no significant influence on the encapsulation rate (P>0.05). The following main effect relationship was determined by the P values of the factors: the ratio of acid to calcium>the concentration of NaCl>the mass ratio of NaALG to $CaCO_3$>the ratio of wall materials to core materials.

After insignificant items were eliminated at a significant level of $\alpha=0.05$, the model (formula 3) can be evolved to obtain:

$$Y_1 = -1459.952 + 168.45017X_3 + 65.075X_1X_4 - 7.93225X_1^2 - 11.37725X_3^2 - 757.35X_4^2 \quad (3).$$

The regression equation $Y_2$ was tested to obtain P<0.05, which indicates that the regression equation is significant, has a good fitting degree, and has practical application. The regression equation coefficients were tested for significance (Table 8), which indicates that the quadratic term $X_1^2$ of the mass ratio of NaALG to $CaCO_3$ and the quadratic term $X_2^2$ of the ratio of wall materials to core materials have extremely significant influence on the average particle size; the concentration $X_4$ of NaCl, the interaction $X_2X_4$ between the ratio of wall materials to core materials and the concentration of NaCl, the interaction $X_3X_4$ between the ratio of acid to calcium and the concentration of NaCl, and the quadratic term $X_4^2$ of the concentration of NaCl have significant influence on the average particle size; and other variables have no significant influence on the average particle size (P>0.05). The following main effect relationship was determined by the P values of the factors: the concentration of NaCl>the ratio of acid to calcium>the ratio of wall materials to core materials>the mass ratio of NaALG to $CaCO_3$.

After insignificant items were eliminated at a significant level of $\alpha=0.05$, the model can be optimized to obtain:

$$Y_2 = 5431.2 + 1034.5X_4 - 275X_2X_4 - 207.5X_3X_4 + 30.39X_1^2 + 32.02X_2^2 + 2264.17X_4^2 \quad (4).$$

To make $Y_1$ the largest and $Y_2$ the smallest, the Design Expert was used for analyzing to obtain the optimal process conditions that the mass ratio of NaALG to $CaCO_3$ was 2.98:1, the ratio of wall materials to core materials was 15:1, the ratio of acid to calcium was 3.17:1, the concentration of NaCl was 0.89%, the encapsulation rate is 74.12%, and the average particle size was 118.1 μm.

To verify the availability and reliability of the regression model obtained in the response surface experiment design, the above optimal preparation parameters were used for verification test. It was assumed that the mass ratio of NaALG to $CaCO_3$ was 3:1, the weight ratio of wall materials to core materials was 15:1, the ratio of acid to calcium was 3:1, and the mass concentration of NaCl was 0.9%, three parallel experiments were carried out to obtain the encapsulation rate of 75.12% and the average particle size of 120 μm, which were close to the predicted values. The results indicate that the equation fits well with the actual conditions, so the process parameters of the endogenous emulsification method for preparing anthocyanin microcapsules obtained by analysis based on the response surface method have high accuracy and reliability and practical reference value.

Further, the influences of three single factors, including the heater temperature, the feed rate and the vacuum pressure, on the microencapsulated powder during spray drying were investigated. Orthogonal experiment design L9 ($3^3$) was carried out according to single factor experiment results to determine the optimal preparation process parameters.

1.1 Determination of Encapsulation Rate

The absorbance values of the separated solution before and after encapsulation can be determined respectively according to UV-Vis spectral absorption characteristics of anthocyanin:

$$\text{Encapsulation rate}/\% = \frac{A_1 - A_2}{A_1} \quad (5)$$

In formula (5), $A_1$ refers to the absorbance of anthocyanin before encapsulation; and $A_2$ refers to the absorbance of anthocyanin after encapsulation.

1.2 Observation for Morphology of Microcapsule Powder and Determination of Particle Size The morphology of dried anthocyanin microcapsules was observed by a scanning electron microscope (SEM) as follows: fixing samples of the anthocyanin microcapsules on a glass slide, plating the samples with a gold film by an ion sputtering apparatus, and then observing the microscopic morphology of the microcapsules under the SEM.

The average particle size and the particle size distribution of anthocyanin microcapsules were determined by a Malvern laser particle size analyzer as follows: dissolving a small amount of dried anthocyanin microcapsules in pure water, then diluting according to a certain proportion, and determining the average particle size and the particle size distribution of anthocyanin microcapsules by the laser particle size analyzer.

1.3 UV-Vis Spectral Analysis of Anthocyanin Microcapsule Powder

A certain amount of anthocyanin microcapsule powder was weighed and dissolved in absolute ethyl alcohol, then was crushed by ultrasonic oscillation to release anthocyanin, and was fully scanned by UV within a wavelength range of 300-800 nm after filtration by a microfiltration membrane, while anthocyanin microcapsules were only dissolved in absolute ethyl alcohol and then were fully scanned by UV in the control group. The anthocyanin microcapsules were dissolved in absolute ethyl alcohol and then were fully scanned by UV; and the control group was anthocyanin.

1.4 Light Stability of Anthocyanin Microcapsule Powder

Control group: 0.05 mg/mL of anthocyanin solution was prepared with a citric acid-disodium hydrogen phosphate buffer solution having pH=2.0 as a solvent.

Experimental group: microcapsules were fully dissolved with 1% DMSO in advance; and then 0.05 mg/mL of anthocyanin solution was prepared with the citric acid-disodium hydrogen phosphate buffer solution having pH=2.0 as the solvent.

The two groups of solutions were sealed and placed under a 50 W fluorescent lamp to investigate the light stability of anthocyanin for 0, 1, 2, 3, 4 and 5 h. The absorbance value was measured by a UV spectrophotometer; and the preservation rate of anthocyanin of the sample was calculated by the following formula:

$$\text{Preservation rate of anthocyanin}/\% = \frac{C_t}{C_0} \quad (6)$$

The photodegradation kinetics analysis for anthocyanin microcapsules and anthocyanin accords with the first-order reaction kinetics equation:

$$\ln(C_t/C_0) = k \times t \quad (7)$$

$$t_{1/2} = \ln 0.5 \times k^{-1} \quad (8).$$

In formulae (6)-(8), $C_0$ refers to an initial absorbance value of the anthocyanin solution; $C_t$ refers to the absorbance value of the solution in light for t hours; $t_{1/2}$ refers to the photodegradation half-life of anthocyanin; and k refers to a degradation reaction rate constant ($h^{-1}$).

1.5 Thermal Stability of Anthocyanin Microcapsule Powder

Control group: 0.05 mg/mL of anthocyanin solution was prepared with the citric acid-disodium hydrogen phosphate buffer solution having pH=2.0 as the solvent.

Experimental group: the anthocyanin microcapsule powder was fully dissolved with 1% DMSO in advance; and then 0.05 mg/mL of anthocyanin solution was prepared with the citric acid-disodium hydrogen phosphate buffer solution having pH=2.0 as the solvent.

The two groups of solutions were sealed and placed in a test tube rack, and were subjected to water bath in dark at 50° C., 60° C., 70° C., 80° C. and 90° C., and were sampled every half hour to determine the changes of the absorbance values within 2.5 h. The preservation rate of anthocyanin was calculated according to formula 1.2; the photodegradation kinetics analysis for anthocyanin microcapsules and anthocyanin accords with the first-order reaction kinetics equation (i.e., formula 7); and the temperature degradation half-life of anthocyanin was calculated according to formula (8).

2. Stability of Anthocyanin Microcapsule Powder in Simulated Human Gastrointestinal Digestive Environment 2.1 Artificial Simulated Gastric Digestion 1.0 g of pepsin was dissolved in 8 mL of 0.1 mol/L HCl to prepare a pepsin solution. Anthocyanin microcapsule powder and anthocyanin powder were weighed and respectively added with trace absolute ethanol to be fully dissolved through vortex oscillation, and then is added with 50 mL of ultrapure water. The solution ethanol was volatilized through a nitrogen blower. Finally, the solution is uniformly dispersed at a high speed to obtain an anthocyanin sample solution. 25 mL of anthocyanin sample solution was taken and adjusted to have a pH of 2.0, then was added with 0.5 mL of pepsin solution, and then was placed in water bath at 37° C. for oscillation at a rotating speed of 100 r/min. The changes of the absorbance values of the sample in the simulated gastric juice for 0, 0.5, 1, 1.5 and 2 h were determined. During reaction, the sample was sealed and stored in dark to prevent the degradation of anthocyanin.

2.2 Artificial Simulated Intestinal Digestion 0.313 g of trypsin and 1.88 g of pig bile salt were mixed and dissolved in 50 mL of 0.1 mol/L NaHCO$_3$ buffer solution to prepare a simulated intestinal solution. A sample digested by stomach for 2 h were placed at −4° C. for 2 h, centrifuged at 3000 r/min for 15 min to remove pepsin. The supernatant was taken and added with 2 mL of a mixed solution of trypsin and pig bile salt, adjusted to have a pH of 6.8 with 0.1 mol/L NaHCO$_3$ buffer solution, and then placed in the water bath at 37° C. for oscillation at a rotating speed of 100 r/min. The changes of the absorbance values of the sample in the simulated intestinal juice for 0, 0.5, 1, 1.5 and 2 h were determined. During the reaction, the sample was sealed and stored in dark to prevent the degradation of anthocyanin.

3. Results and Analysis 3.1 Analysis of Single Factor Experiment Results of Spray Drying 3.1.1 Influence of Heater Temperature on Particle Size and Encapsulation Rate of Anthocyanin Microcapsules In the setting of low-temperature spray drying parameters, at a constant feed rate of 12 r/min and a constant vacuum pressure of 0.03 MPa, the influence of heater temperature on the average particle size and the encapsulation rate of anthocyanin microcapsule powder is shown in FIG. 2.

Figure 2:
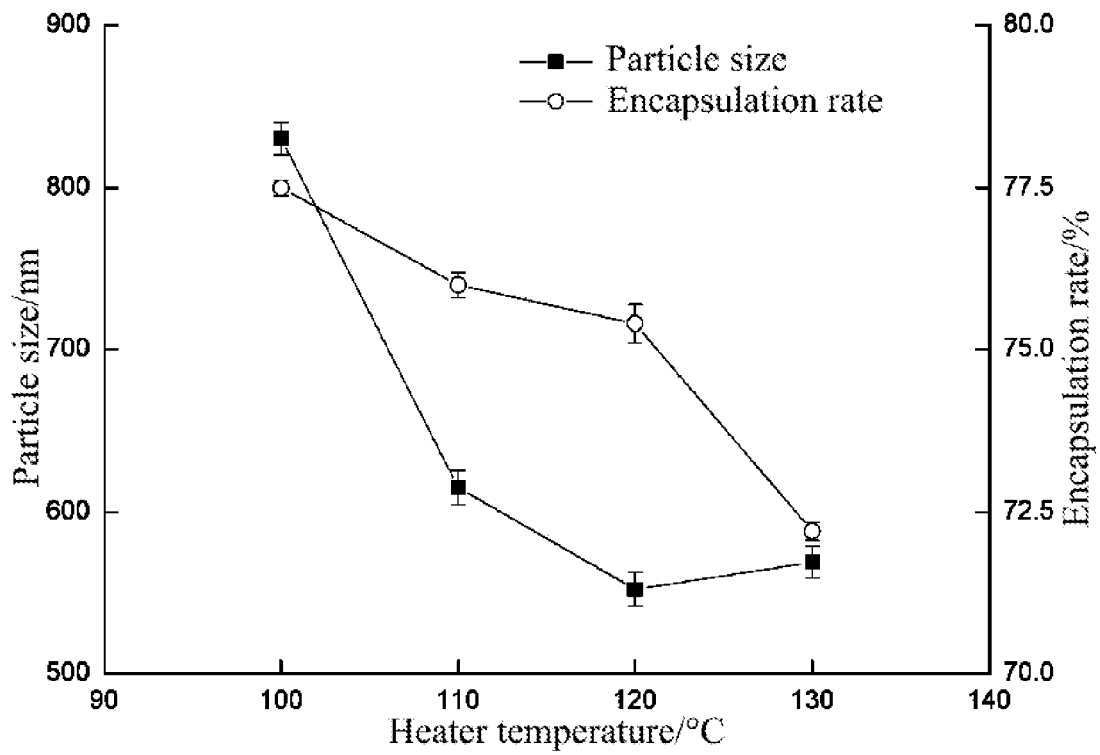
FIG. 2 shows influence of heater temperature on an average particle size and an encapsulation rate of anthocyanin microcapsule powder in embodiment 4 of the present invention.

FIG. 2 shows that with the rise of temperature, the average particle size of anthocyanin microcapsule powder decreases first and then increases, and the encapsulation rate shows a downward trend. When the encapsulation rate fluctuates slightly with the change of temperature, the change of particle size should be mainly considered. When the heater temperature is 120° C., the average particle size of microcapsules reaches a minimum value of 552.3 nm; the encapsulation rate is 75.4%; at this time, the temperatures of a feed inlet and a feed outlet are 70.2° C. and 64.8° C., respectively; and after this, the average particle size increases with the rise of heater temperature. Perhaps the temperatures of the feed inlet and the feed outlet are too low when the heater temperature is too low, the microencapsulation time is long, the solvent is evaporated slowly, the fluidity is poor, and the microcapsules are easy to regain moisture, so that the microcapsule particles have uneven aggregation size and relatively wide particle size distribution. When the heater temperature is too high, the solvent is evaporated too fast to break the capsule wall, thereby influencing the stability and bioactivity of anthocyanin microcapsules. Therefore, the optimal heater temperature in the spray drying method for preparing anthocyanin microcapsule powder is determined to be 120° C.

Figure 3:
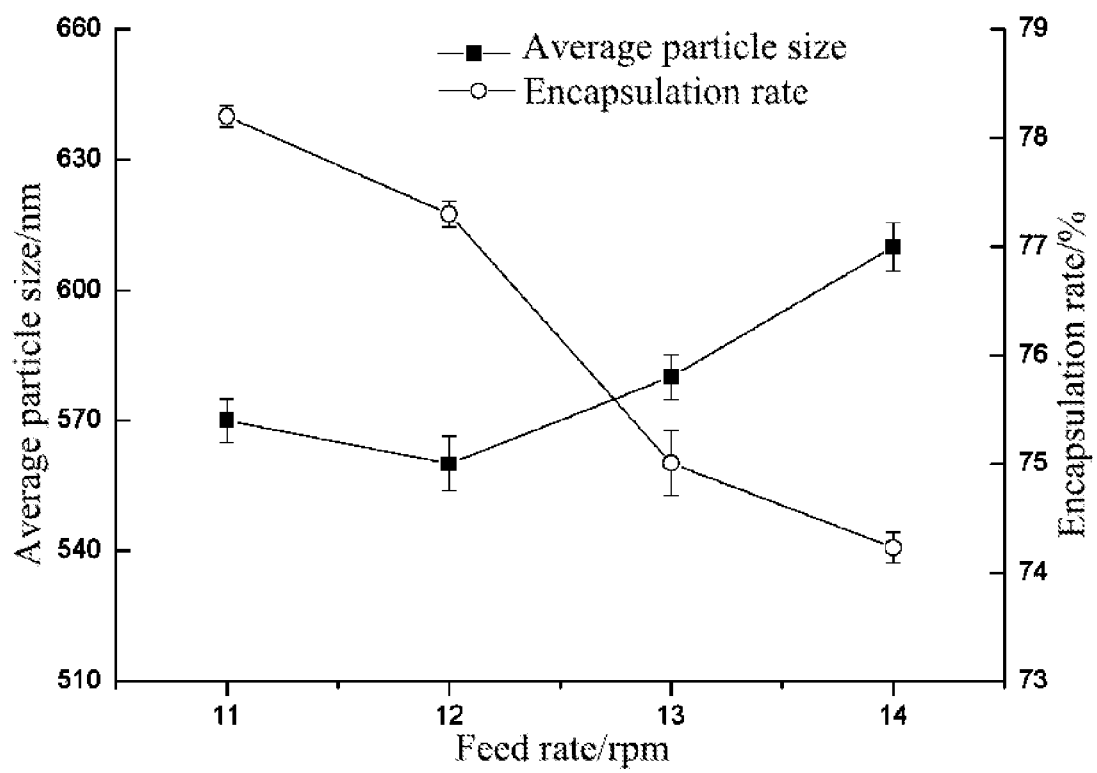
FIG. 3 shows influence of a feed rate on the average particle size and the encapsulation rate of the anthocyanin microcapsule powder in embodiment 4 of the present invention.

3.1.2 Influence of Feed Rate on Particle Size and Encapsulation Rate of Anthocyanin Microcapsule Powder In the setting of low-temperature spray drying parameters, at a vacuum temperature of 0.03 MPa and a constant heater temperature of 120° C., the influence of feed rate on the average particle size and the encapsulation rate of anthocyanin microcapsule powder is shown in FIG. 3.

FIG. 3 shows that with the increase of feed rate, the average particle size of anthocyanin microcapsule powder decreases first and then increases, and the encapsulation rate shows a downward trend. In view of the changing trend and fluctuation of the particle size and the encapsulation rate, the average particle size is selected as the main reference. When the feed rate reaches 12 r/min, the average particle size reaches a minimum value of 571.5 nm; the encapsulation rate is 77.3%; and after this, the average particle size increases with the increase of feed rate. Perhaps the feed rate is too high during spray drying, the flow of samples is too high, and more samples enter an atomizer to reduce the heat and mass transfer efficiency between the samples and hot air, so that the samples are not sufficiently dried to cause the aggregation of microcapsule particles, thereby influencing the particle size of anthocyanin microcapsules. Therefore, the optimal feed rate in the spray drying method for preparing anthocyanin microcapsule powder is determined to be 12 r/min.

Figure 4:
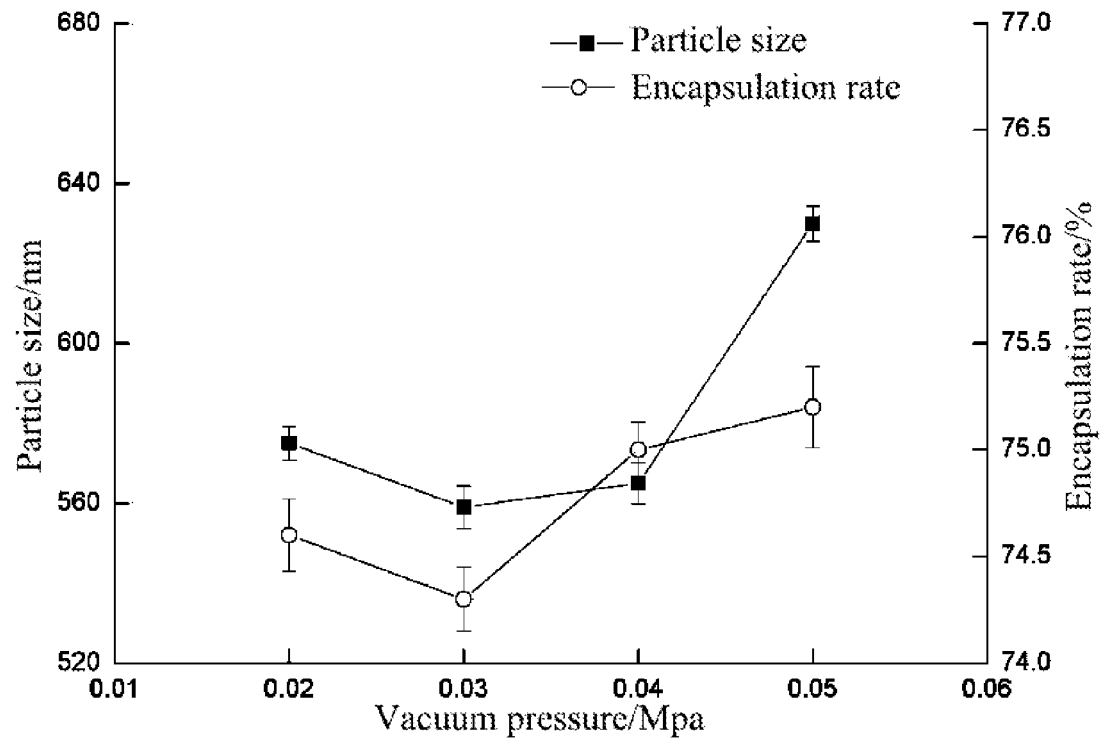
FIG. 4 shows influence of vacuum pressure on the average particle size and the encapsulation rate of the anthocyanin microcapsule powder in embodiment 4 of the present invention.

3.1.3 Influence of Vacuum Pressure on Particle Size and Encapsulation Rate of Anthocyanin Microcapsules In the setting of low-temperature spray drying parameters, at a constant heater temperature of 120° C. and a constant feed rate of 12 r/min, the influence of vacuum pressure on the average particle size and the encapsulation rate of anthocyanin microcapsules is shown in FIG. 4.

FIG. 4 shows that with the increase of vacuum pressure, the average particle size and the encapsulation rate of anthocyanin microcapsules decrease first and then increase; in view of the changing trend and fluctuation of the particle size and the encapsulation rate, the average particle size is selected as the main reference; at 0.03 MPa, the average particle size is only 560.1 nm, and the encapsulation rate is 74.3%; and after this, the average particle size increases with the increase of vacuum pressure. Perhaps the relatively small vacuum pressure influences the solvent evaporation speed and the particle forming speed, a distance between the feed inlet and the feed outlet is relatively short, so that the samples are not dried and formed in time. When the vacuum pressure is too high, the capsule wall fails to bear the pressure, so that the capsule wall is broken and the core materials flow out. Therefore, the optimal vacuum pressure in the spray drying method for preparing anthocyanin microcapsules is determined to be 0.03 MPa.

3.2 Analysis of Orthogonal Experiment Results of Spray Drying

According to the single factor experiment results, designs and results of orthogonal experiment are as shown in Table 9.

TABLE 9

Designs and Results of Orthogonal Experiment

| Test number | A | Vacant column | B | C | Average particle size/nm |
|---|---|---|---|---|---|
| 1 | 1 | 1 | 1 | 1 | 567.1 ± 10.9 |
| 2 | 1 | 2 | 2 | 2 | 697.8 ± 10.2 |
| 3 | 1 | 3 | 3 | 3 | 570.8 ± 13.6 |
| 4 | 2 | 1 | 2 | 3 | 771.0 ± 12.9 |
| 5 | 2 | 2 | 3 | 1 | 743.4 ± 14.5 |
| 6 | 2 | 3 | 1 | 2 | 726.7 ± 11.1 |
| 7 | 3 | 1 | 3 | 2 | 659.9 ± 13.9 |
| 8 | 3 | 2 | 1 | 3 | 623.3 ± 11.8 |
| 9 | 3 | 3 | 2 | 1 | 648.9 ± 12.9 |
| K1 | 1835.7 | 1998 | 1917.1 | 1959.4 | |
| K2 | 2241.1 | 2064.5 | 2117.7 | 2084.4 | |
| K3 | 1932.1 | 1946.4 | 1974.1 | 1965.1 | |
| k1 | 611.9 | 666 | 639.03 | 653.13 | |
| k2 | 747.03 | 688.17 | 705.9 | 694.8 | |
| k3 | 644.03 | 652.13 | 658.03 | 655.03 | |
| Range R | 135.13 | 36.03 | 66.89 | 41.67 | |
| Order of factors | | ABC | | | |
| Optimal solution | | $A_2B_2C_2$ | | | |

Analysis for the results of orthogonal experiment in Table 9 shows that the order of influencing factors is the heater temperature A, the feed rate B and the vacuum pressure C. The optimal solution is that the heater temperature is 120° C., the feed rate is 12 r/min, and the vacuum pressure is 0.03 MPa. According to the verification test, when the samples are spray-dried in the optimal conditions, the average particle size of anthocyanin microcapsule powder is only 558.2 nm, and the encapsulation rate is 75.12%, which are better than those in in other solution groups of the table. Therefore, $A_2B_2C_2$ is the optimal experimental condition for the spray drying of anthocyanin microcapsules.

3.3 Morphology and Particle Size of Anthocyanin Microcapsules

3.3.1 Morphology of Anthocyanin Microcapsules

Figure 5:
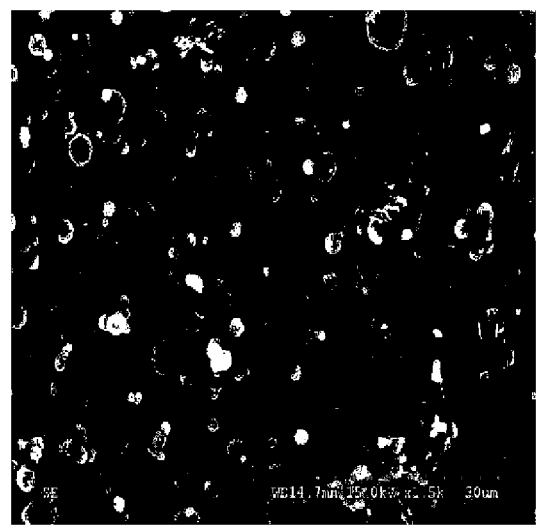
FIG. 5 shows morphology of the anthocyanin microcapsule powder in embodiment 4 of the present invention under a scanning electron microscope.

The microcapsule morphology in FIG. 5 shows that the spray-dried anthocyanin microcapsule powder has uniformly distributed anthocyanin microcapsules and complete particles, has a circular external structure with agglomerates in different sizes, and has the characteristics of spray-dried powder.

3.3.2 Particle Size of Anthocyanin Microcapsules

Figure 6:
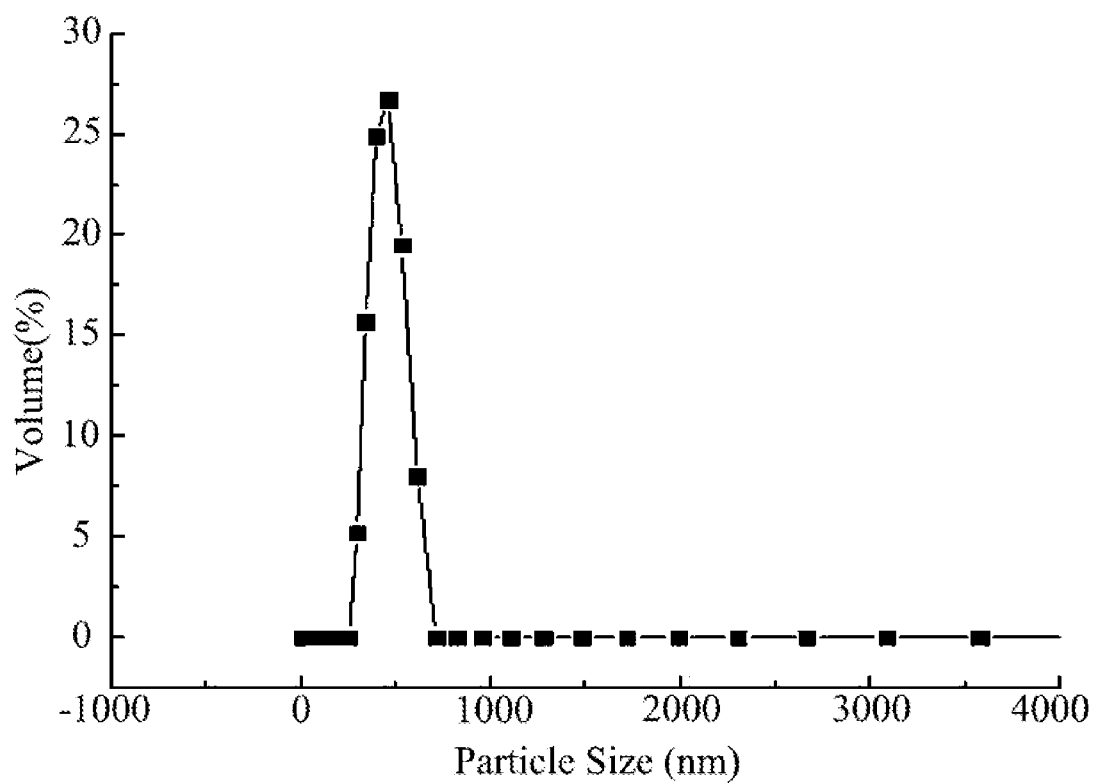
FIG. 6 shows the particle size distribution of the anthocyanin microcapsule powder in embodiment 4 of the present invention.

As shown in FIG. 6, the spray-dried anthocyanin microcapsule powder has powder form, good sphericity, uniform size, uniform particle size distribution, and the average particle size up to 558.2 nm. In conclusion, the spray drying method is beneficial to the preparation of encapsulated products, requires relatively short time for preparation to prevent the samples from being heated for a long time, and can effectively reduce the particle size of microcapsules to make the particle size distribution more concentrated.

3.4 UV-Vis Spectral Characteristics of Anthocyanin Microcapsule Powder

Figure 7A:
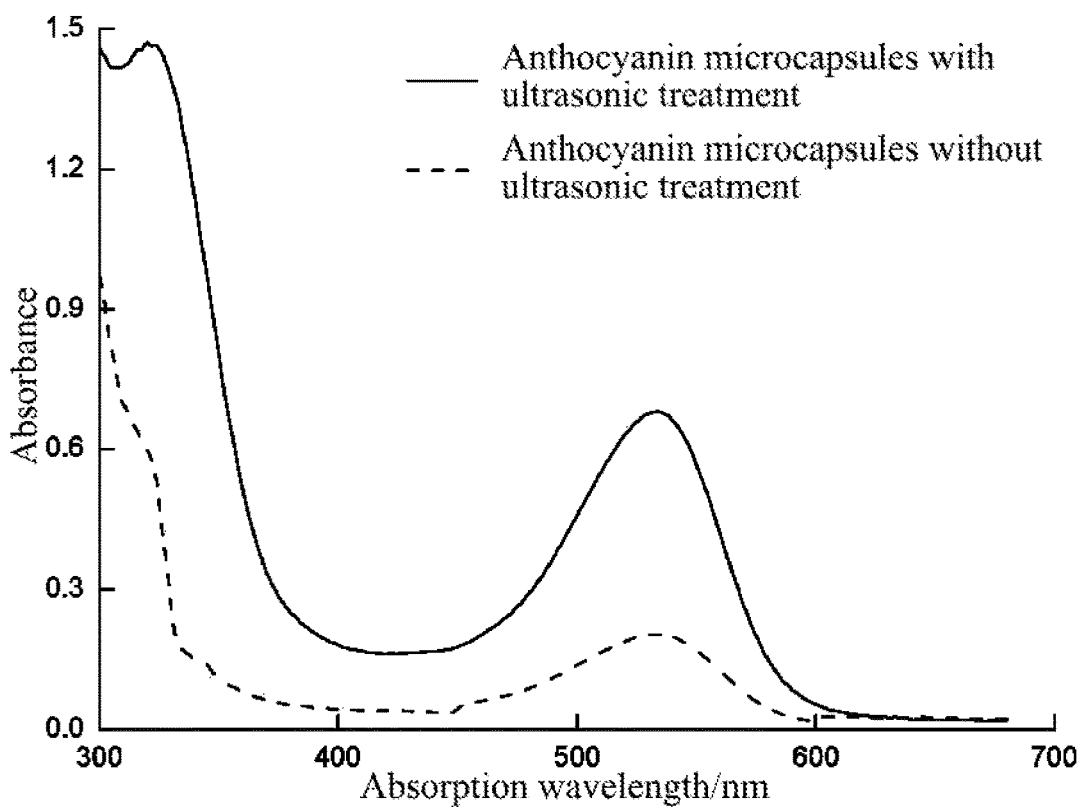
FIG. 7a shows the ultraviolet-visible (UV-Vis) spectral characteristics of the anthocyanin microcapsule powder without ultrasonic treatment and with ultrasonic treatment in embodiment 4 of the present invention.
Figure 7B:
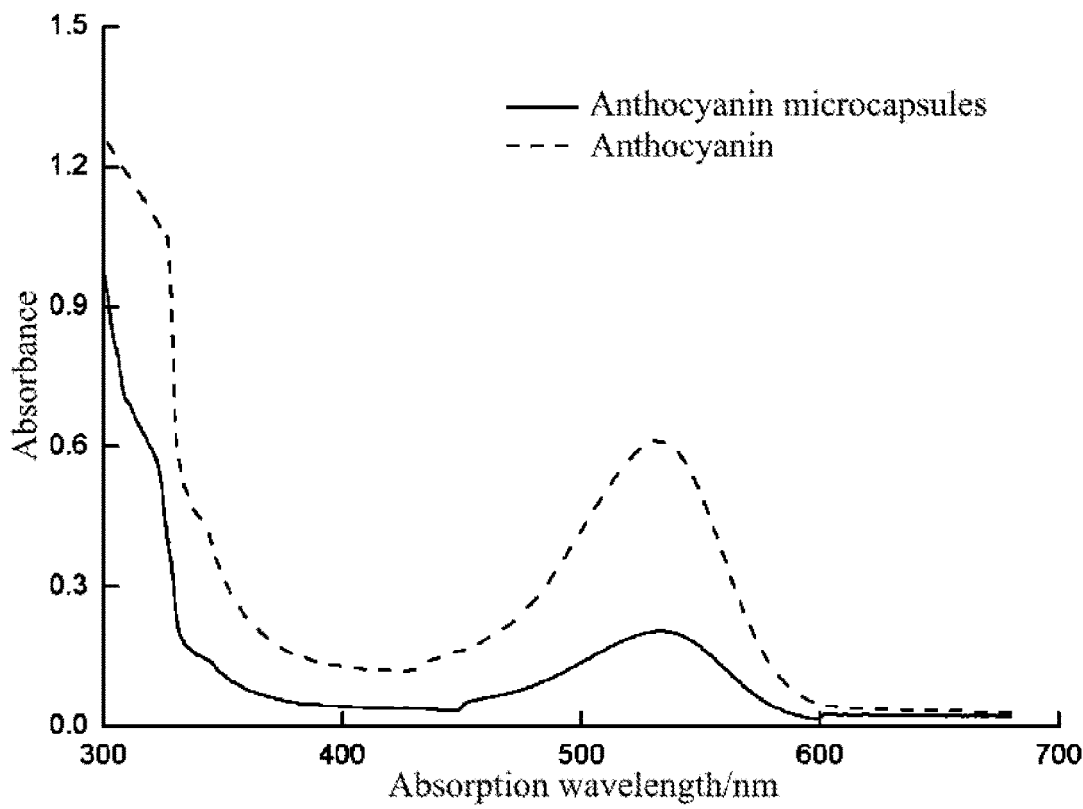
FIG. 7b shows UV-Vis spectral characteristics of the anthocyanin microcapsule powder and anthocyanin in embodiment 4 of the present invention.

FIGS. 7a-7b show that the ultrasonically crushed anthocyanin microcapsule powder and anthocyanin samples have a maximum spectral absorption peak at 542 nm, which accords with the visible light absorption characteristics of anthocyanin within a maximum anthocyanin absorption region of 465-550 nm; and at this time, the encapsulation rate of anthocyanin microcapsule powder is 75.12%, and the anthocyanin is well encapsulated in microcapsules basically without loss.

3.5 Influence of Light on Stability of Anthocyanin Microcapsule Powder

Figure 8A:
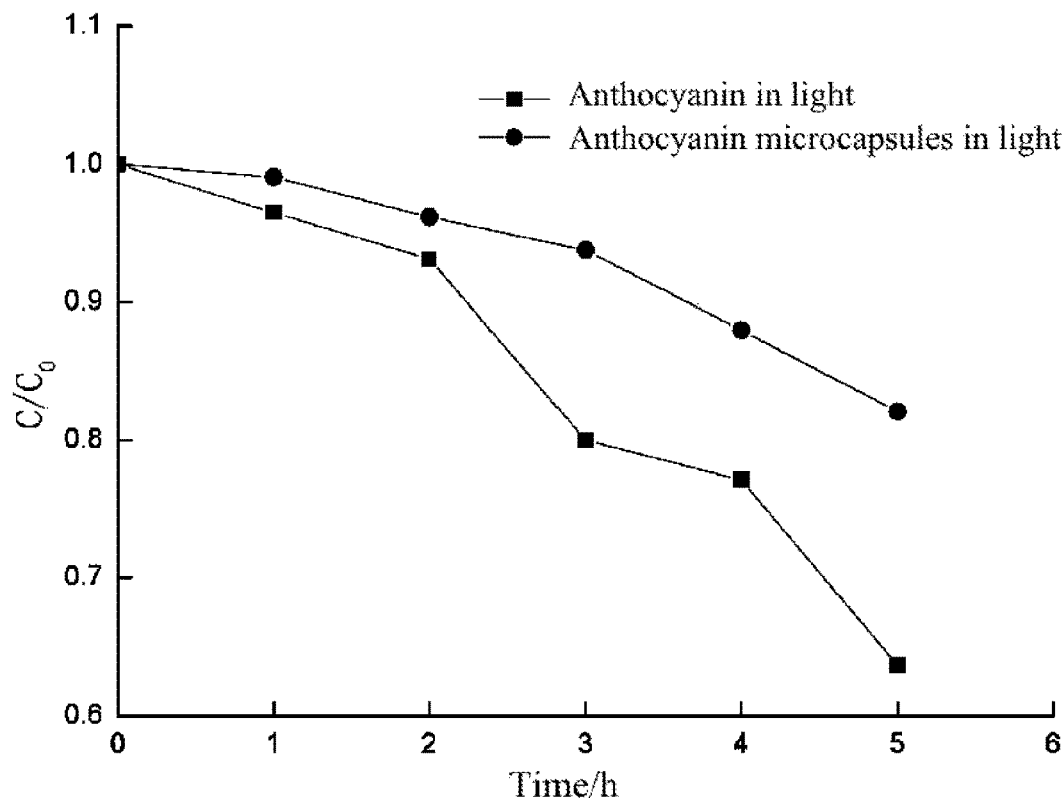
FIG. 8a shows influence of light on the stability of the anthocyanin microcapsule powder and the anthocyanin in embodiment 4 of the present invention.
Figure 8B:
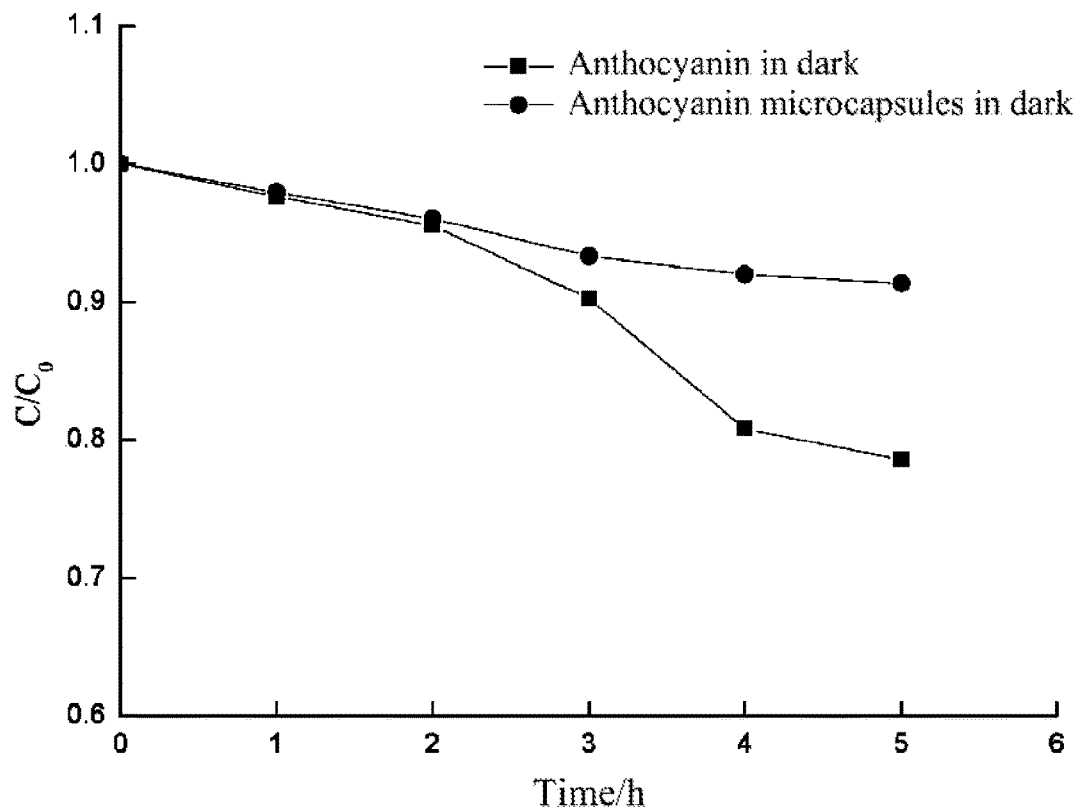
FIG. 8b shows influence of dark on the stability of the anthocyanin microcapsule powder and the anthocyanin in embodiment 4 of the present invention.

FIGS. 8a-8b show that the preservation rates of anthocyanin microcapsule powder are 93.8% and 82.1%, and the preservation rates of anthocyanin are 80.0% and 63.7%, respectively, in light for 3 h and 5 h. The results imply that the light stability of anthocyanin microcapsule powder is apparently higher than that of anthocyanin, which indicates that sodium alginate can be taken as the wall material for preparing microcapsules to effectively protect the core material of anthocyanin. The preservation rates of anthocyanin and anthocyanin microcapsules are 78.6% and 91.4%, respectively, in dark for 5 h. The results show that microencapsulation can increase the preservation rate of anthocyanin. Comparison of the preservation rates of anthocyanin and anthocyanin microcapsules in light and dark show that light can accelerate the degradation of anthocyanin, while the microencapsulation can enhance the tolerance of anthocyanin to light, thereby improving the stability of anthocyanin microcapsule powder.

Figure 9:
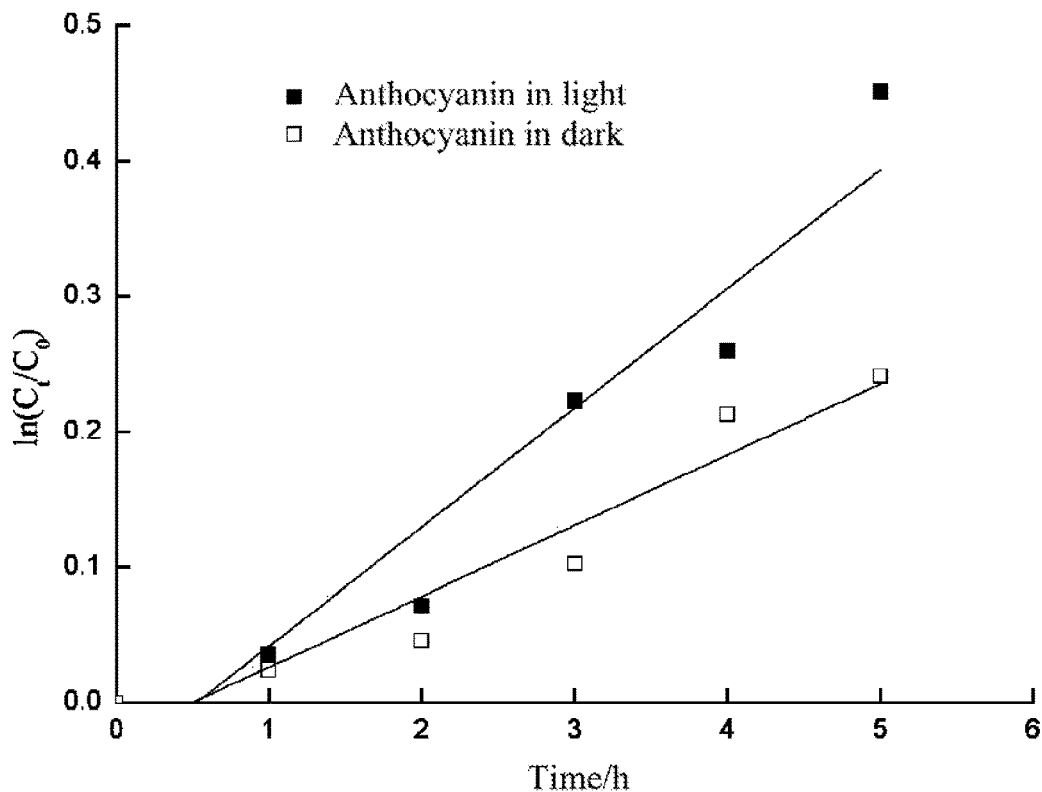
FIG. 9 shows influence of light on degradation of the anthocyanin microcapsule powder and the anthocyanin in embodiment 4 of the present invention.
Figure 10:
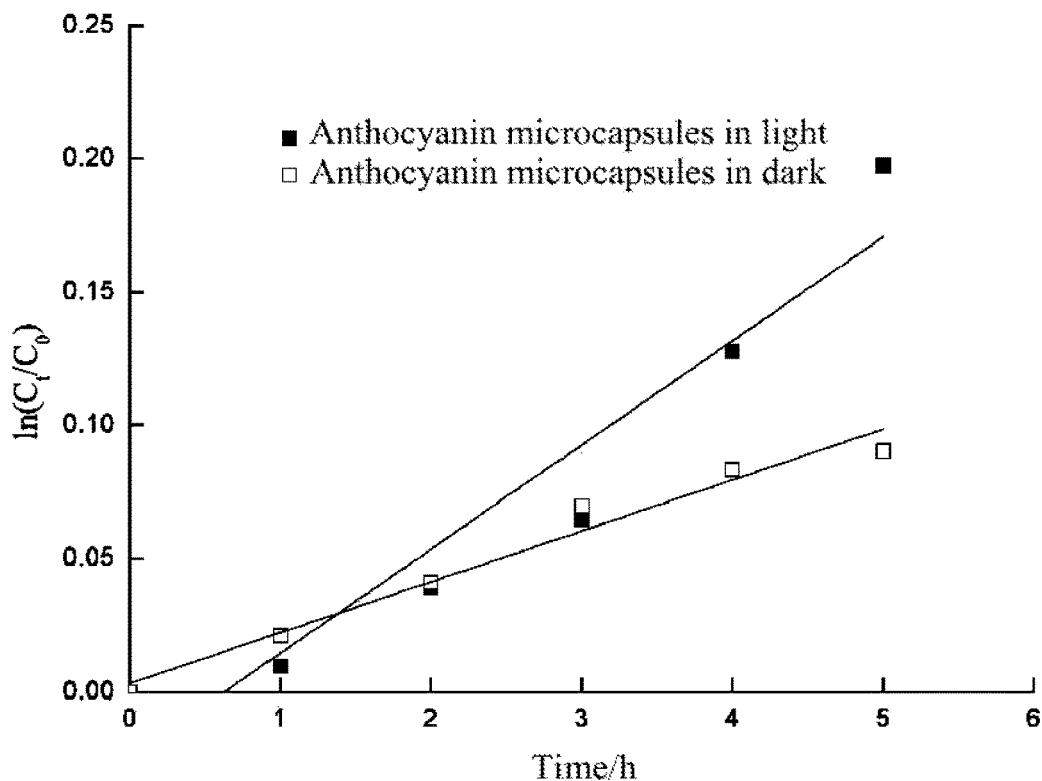
FIG. 10 shows influence of dark on the degradation of the anthocyanin microcapsule powder and the anthocyanin in embodiment 4 of the present invention.

Further, a regression fitting line with the light time as the abscissa and $-Ln(C/Co)$ as the ordinate is available; and the degradation of anthocyanin and anthocyanin microcapsules by light is as shown in FIGS. 9 and 10. The linear regression analysis shows that $-Ln(Ct/Co)$ has a good linear relationship with time. The photodegradation kinetics of anthocyanin and anthocyanin microcapsules accord with the first-order kinetic reaction; and the degradation kinetic parameters are as shown in Table 10.

TABLE 10

Photodegradation Kinetic Parameters of Anthocyanin and Anthocyanin Microcapsule Powder

| Group name | Treatment mode | k(h$^{-1}$) | t$_{1/2}$(h) | R$^2$ |
|---|---|---|---|---|
| Anthocyanin | In light | 0.060212 | 11.51 | 0.9247 |
| Anthocyanin | In dark | 0.0366 | 18.93 | 0.9322 |
| Anthocyanin microcapsule powder | In light | 0.024434 | 28.36 | 0.9188 |
| Anthocyanin microcapsule powder | In dark | 0.020708 | 33.47 | 0.9728 |

Table 10 shows that the first-order reaction rate constants k of anthocyanin and anthocyanin microcapsule powder are increased and the half-lives t$_{1/2}$(h) are decreased in the light conditions compared with the dark conditions, which indicates that the anthocyanin is unstable in the light conditions, and the dark conditions are more conducive to preservation. In the light and dark conditions, the half-life t$_{1/2}$(h) of anthocyanin microcapsule powder is greater than that of anthocyanin, which indicates that anthocyanin of microencapsulated powder is more stable because of no direct exposure to light due to the protection of wall materials.

3.6 Influence of Temperature on Stability of Anthocyanin Microcapsule Powder

Figure 11A:
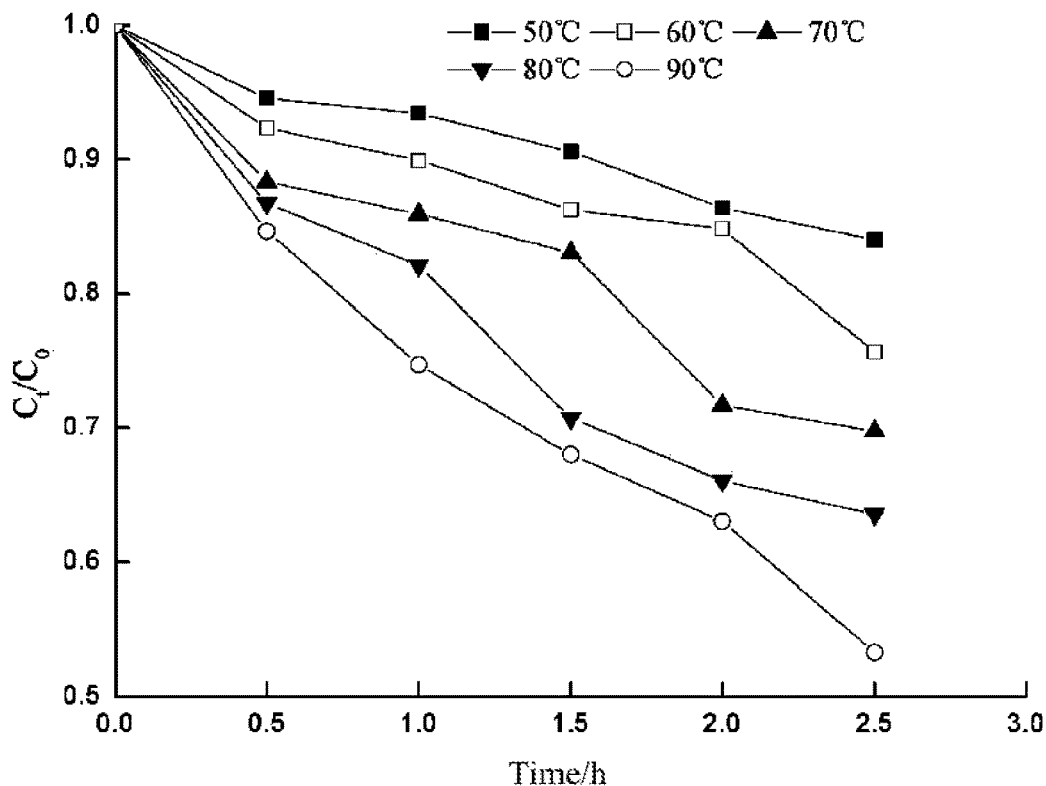
FIG. 11a shows influence of temperature on the stability of anthocyanin.
Figure 11B:
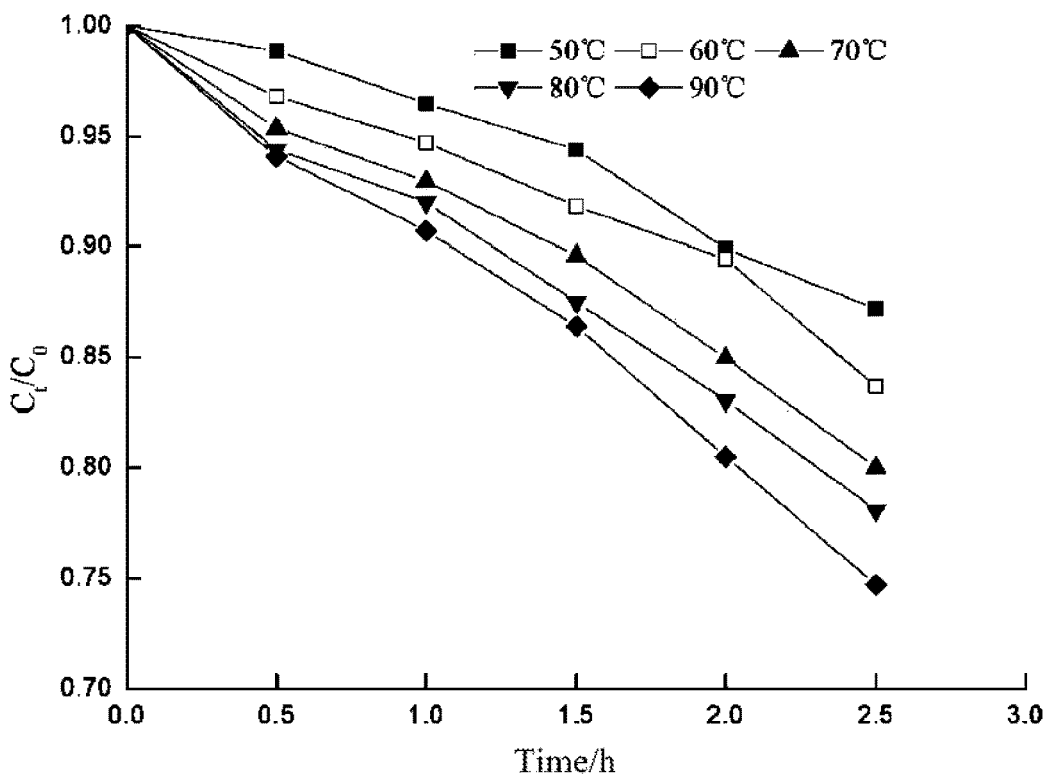
FIG. 11b shows influence of temperature on the stability of anthocyanin microcapsule powder in embodiment 4 of the present invention.

FIGS. 11a-11b shows that anthocyanin and anthocyanin microcapsule powder are thermally degraded in different degrees at high temperature. FIG. 10a shows that the preservation rate of anthocyanin decreases rapidly after the samples are heated at high temperature for 1 h, and the preservation rate is only 53.3% when the samples are heated at 90° C. for 2.5 h; and the preservation rate of anthocyanin microcapsule powder decreases gradually when the samples are heated at high temperature for 1.5 h, and the preservation rate is 74.7% when the samples are heated at 90° C. for 2.5 h. Therefore, with the increase of heating time and temperature, compared with microencapsulated anthocyanin, the thermal degradation of anthocyanin is more significant, i.e., the thermal stability of microencapsulated anthocyanin at high temperature is higher, probably because the microencapsulated anthocyanin is protected by sodium alginate wall materials so that the structure is not directly destroyed.

Figure 12:
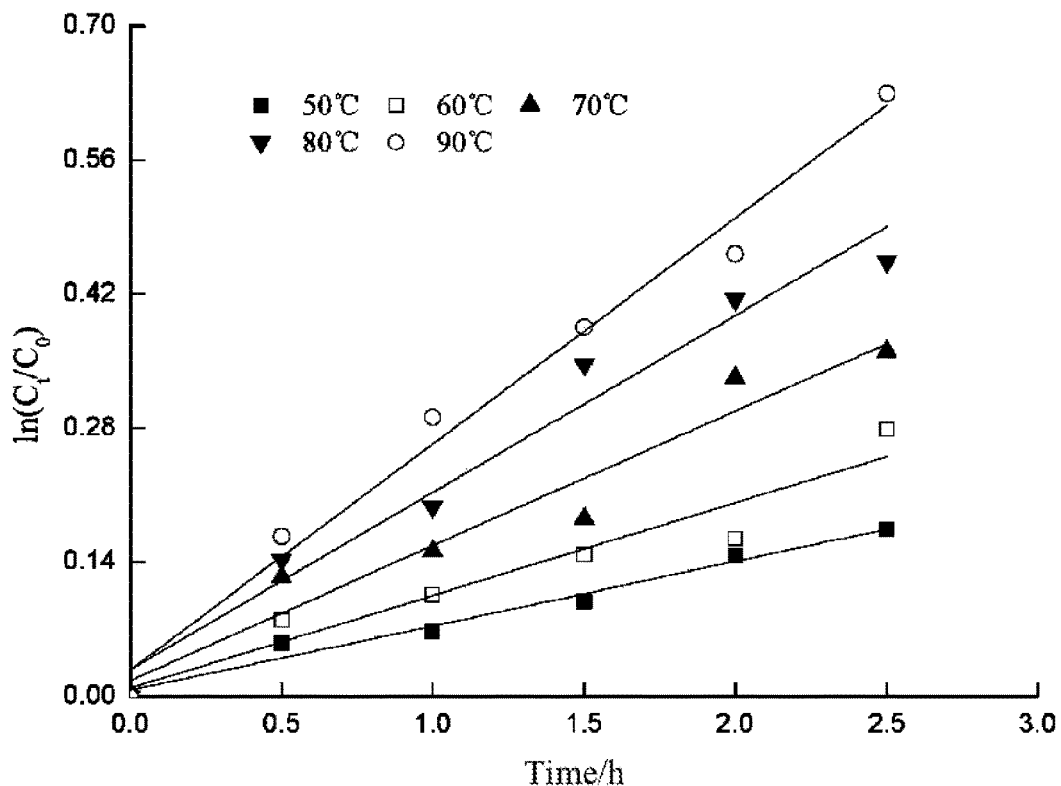
FIG. 12 shows influence of light on thermal degradation of anthocyanin.

Further, the regression fitting line with the heating time as abscissa and $-Ln(C_t/C_0)$ as ordinate is shown in FIGS. 11-12. Linear regression analysis shows that $-Ln(C_t/C_0)$ has a good linear relationship with time; the photodegradation kinetics of anthocyanin and anthocyanin microcapsules all accord with the first-order kinetic reaction; and the degradation kinetic parameters are as shown in Table 11.

TABLE 11

Thermal Degradation Kinetic Parameters of Anthocyanin and Anthocyanin Microcapsule Powder

| Group name | Temperature/° C. | k(h$^{-1}$) | t$_{1/2}$(h) | R$^2$ |
|---|---|---|---|---|
| Anthocyanin | 50 | 0.077732 | 8.92 | 0.979 |
|  | 60 | 0.111732 | 6.20 | 0.9355 |
|  | 70 | 0.166916 | 4.15 | 0.9481 |
|  | 80 | 0.220418 | 3.14 | 0.9689 |
|  | 90 | 0.272848 | 2.54 | 0.9854 |
| Anthocyanin microcapsule powder | 50 | 0.040938 | 16.93 | 0.97 |
|  | 60 | 0.060624 | 11.43 | 0.9742 |
|  | 70 | 0.082396 | 8.41 | 0.9677 |
|  | 80 | 0.09588 | 7.23 | 0.9778 |
|  | 90 | 0.10841 | 6.39 | 0.9555 |

Figure 13:
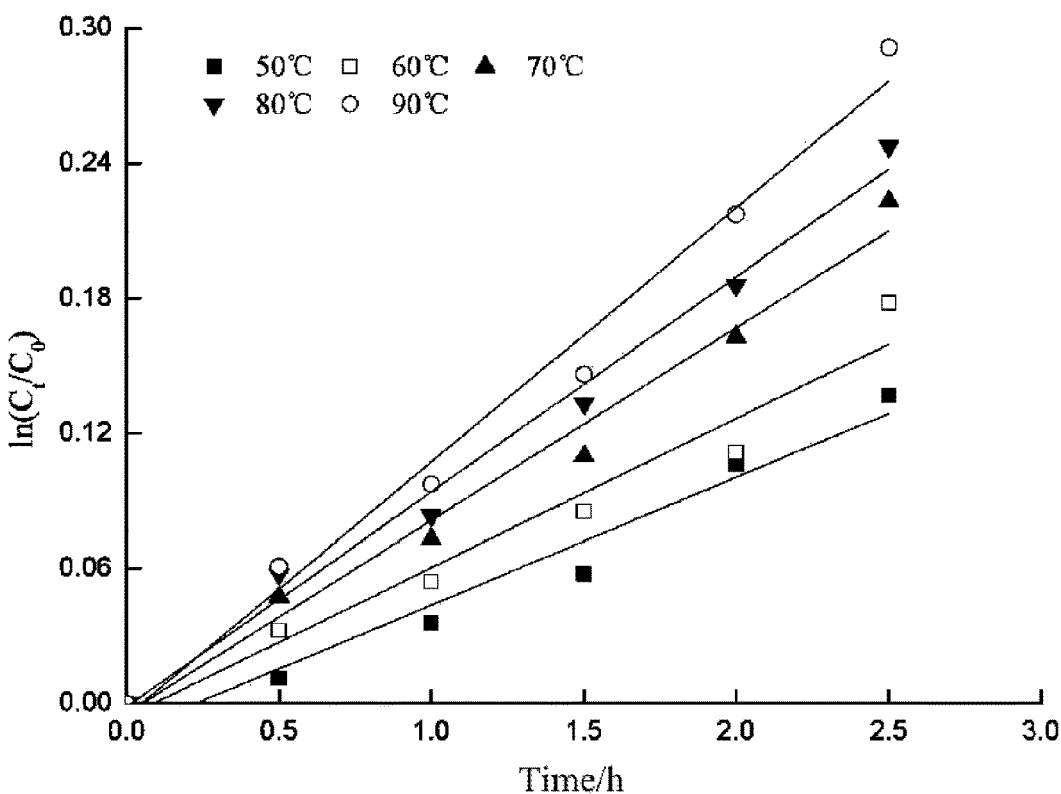
FIG. 13 shows influence of light on thermal degradation of anthocyanin in embodiment 4 of the present invention.

As shown in FIGS. 12-13, with the rise of temperature, the first-order reaction rate constants k of anthocyanin and anthocyanin microcapsule powder increase, while the half-life t$_{1/2}$(h) decreases, which indicates that the thermal stability of anthocyanin and anthocyanin microcapsules decreases and the thermal degradation rate is high at high temperature. At the same temperature, the thermal degradation rate constant k (0.040938) of anthocyanin microcapsules is smaller than that (0.077732) of anthocyanin, while the half-life t$_{1/2}$(h)(16.93 h) is greater than that t$_{1/2}$(h) (8.92 h) of anthocyanin, which indicates that the microencapsulated anthocyanin is more stable than anthocyanin at high temperature and also reflects the effectiveness of encapsulating anthocyanin through microencapsulation.

Figure 14:
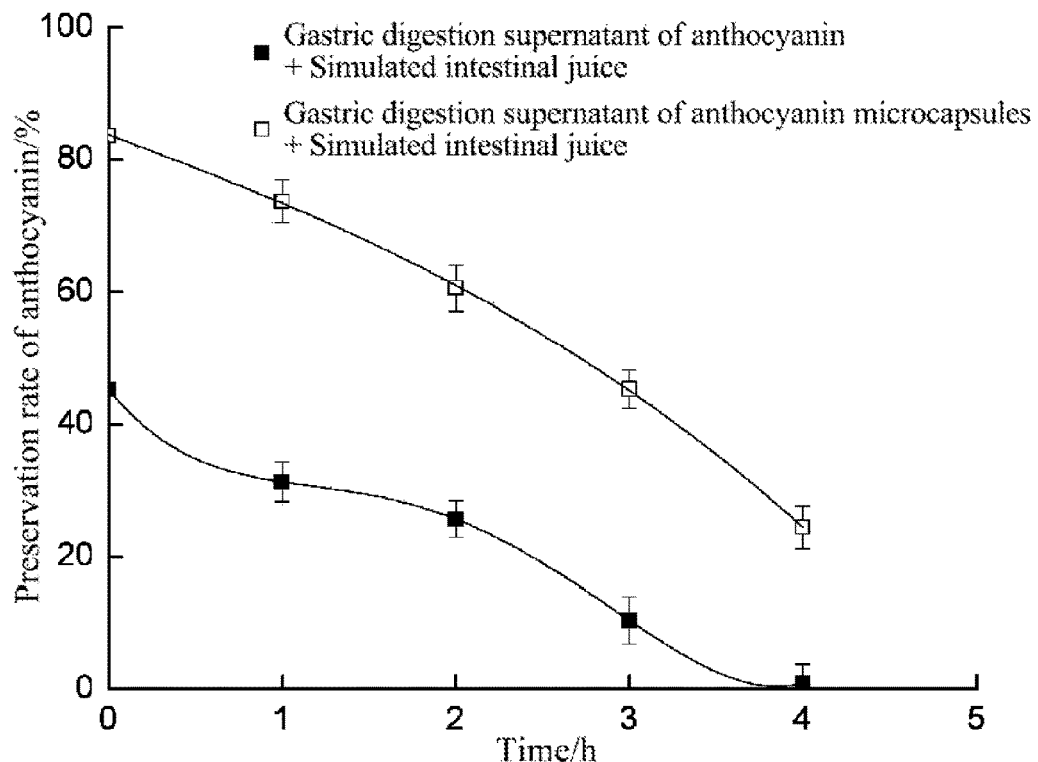
FIG. 14 shows a preservation rate of anthocyanin in artificial simulated gastric juice.

3.7 Stability of Anthocyanin Microcapsule Powder in Simulated Human Gastrointestinal Digestive Environment FIG. 14 shows that anthocyanin and anthocyanin microcapsule powder are degraded in different degrees after digestion in artificial simulated gastric juice. After digestion in gastric juice for 2 h, the preservation rates of anthocyanin and anthocyanin microcapsule powder are 45.3% and 83.7%, respectively. In acid condition of artificial simulated gastric juice, the wall material structure is stable to protect the core materials better, so the microencapsulated anthocyanin had higher stability and better sustained-release effect. It is documented that the microcapsules can modify the structure of samples to change the release rate, so anthocyanin microcapsules are more resistant to acidic environment, and the preservation rate is relatively higher than that of anthocyanin; and more than half of anthocyanin can enter the intestinal environment.

Figure 15:
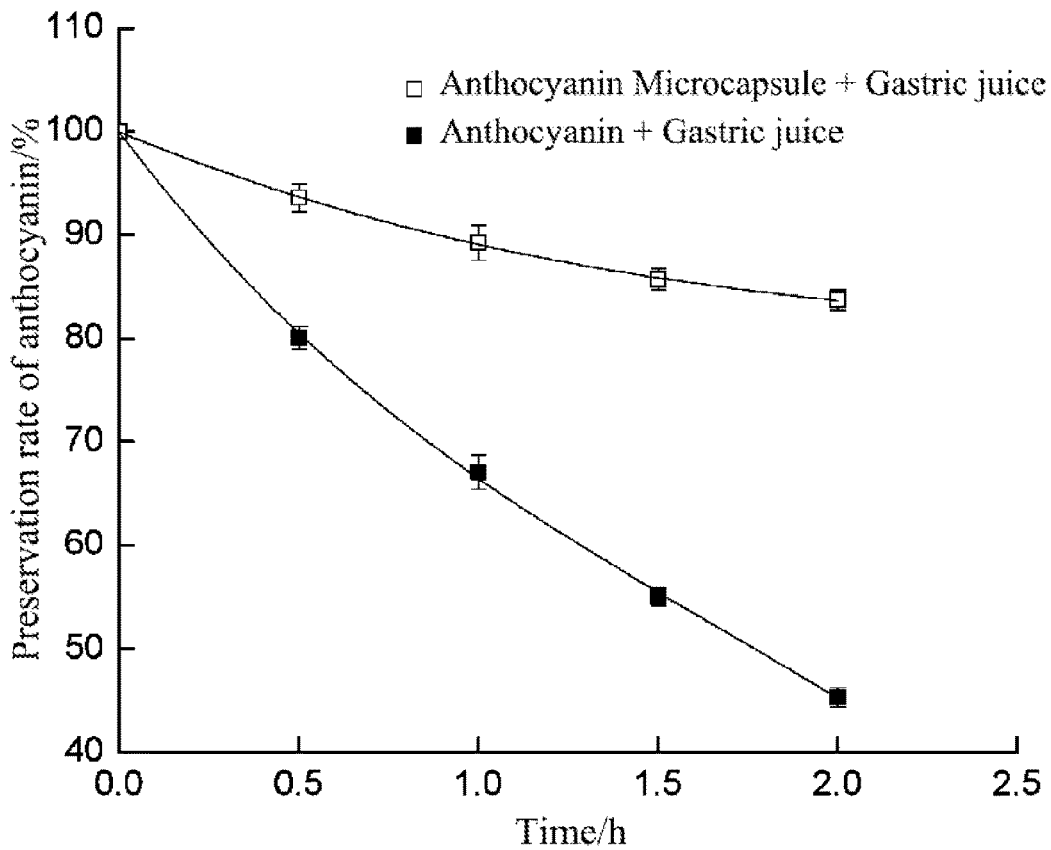
FIG. 15 shows a preservation rate of anthocyanin in artificial simulated intestinal juice.

In the existing literature, the simulated gastric digestion time is generally 2 h, and can also be 0.5-1 h or even 5 h. Table 12 shows that the preservation rate of the samples tends to be stable after gastric digestion for 2 h, so the enzyme-removed samples after gastric digestion for 2 h are taken as the initial samples of simulated intestinal digestion; and after artificial intestinal digestion for 4 h, the artificial simulated intestinal juice has a pH of 6.8. FIG. 15 shows that anthocyanin and anthocyanin microcapsule powder are significantly degraded in the artificial simulated intestinal environment; and after gastric digestion for 2 h and intestinal digestion for 4 h, the preservation rates of anthocyanin and anthocyanin microcapsule powder are 0.9% and 24.4%, respectively, which indicates that microencapsulation can better control the release of anthocyanin and thus can inhibit the degradation of anthocyanin.

TABLE 12

Preservation Rates of Anthocyanin and Anthocyanin Microcapsule Powder after Artificial Simulated Digestion

|  | Treatment mode | Preservation rate (%) |
|---|---|---|
| Simulated gastric digestion pH = 2.0 27° C., 2 h | Anthocyanin + Simulated gastric juice | 45.3 ± 0.6 |
|  | Anthocyanin Microcapsule + Simulated gastric juice | 83.7 ± 2.7 |
| Simulated intestinal digestion 37° C. 4 h | Gastric digestion supernatant of anthocyanin + Simulated intestinal juice | 0.9 ± 0.1 |
|  | Gastric digestion supernatant of anthocyanin microcapsules + Simulated intestinal juice | 24.4 ± 1.3 |

The above experiments are analyzed to show that the microencapsulated anthocyanin has relatively strong stability and relatively high preservation rate in gastric environment (pH=2.0), and the stabilities of the anthocyanin microcapsule powder in artificial simulated gastric and intestinal juice are all higher than those of anthocyanin.

The light, temperature and artificial simulated gastric and intestinal juice stabilities before and after microencapsulation of anthocyanin are compared to show that the stability of microencapsulated anthocyanin is apparently better than that of anthocyanin. The protection effect of sodium alginate as the wall material is combined with the excellent characteristics of spray-dried microcapsules such as powder form, fine texture, good fluidity and compact structure, to isolate the contact between anthocyanin and the external environment to a certain extent, thereby delaying the release of anthocyanin. During actual production, spray drying can continuously feed, has high production efficiency, saves cost, and is suitable for large-scale continuous production.

In the present experiment, sodium alginate was used as the wall material to prepare wet anthocyanin microcapsules by the endogenous emulsification method; then, the influence of spray drying process on microencapsulated wet anthocyanin was investigated; single factor test and orthogonal test were carried out to obtain the optimal process parameters in the spray drying of anthocyanin microcapsules as follows: the heater temperature was 120° C., the feed rate was 12 r/min, the vacuum pressure was 0.03 MPa, the average particle size of anthocyanin microcapsules was 558.2 nm, and the encapsulation rate was 75.12%.

The study results show that the photodegradation stabilities of anthocyanin before and after microencapsulation all accord with the first-order reaction kinetics equation, and the preservation rate is higher in dark than in light. In addition, the stabilities of anthocyanin microcapsules are all higher than those of anthocyanin in light and dark. The thermal degradation stabilities of anthocyanin before and after microencapsulation also accord with the first-order reaction kinetics equation, and the preservation rates decrease with the rise of temperature, but the temperature stability of anthocyanin microcapsules is higher than that of anthocyanin. The stabilities of anthocyanin microcapsules in the artificial simulated gastric and intestinal juice are higher than those of anthocyanin.

According to the present invention, sodium alginate is used as the wall material to prepare wet anthocyanin microcapsules; then, the influence of spray drying process on the microencapsulated wet anthocyanin is investigated; single factor test and orthogonal test are carried out to obtain the optimal process parameters in the spray drying of anthocyanin microcapsules as follows: the heater temperature is 120° C., the feed rate is 12 r/min, the vacuum pressure is 0.03 MPa, the average particle size of anthocyanin microcapsule powder is 558.2 nm, and the encapsulation rate is 75.12%.

Meanwhile, according to the present invention, the photodegradation stabilities of anthocyanin before and after microencapsulation all accord with the first-order reaction kinetics equation, and the preservation rate is higher in dark than in light. In addition, the stabilities of anthocyanin microcapsule powder are all higher than those of anthocyanin in light and dark. The thermal degradation stabilities of anthocyanin before and after microencapsulation also accord with the first-order reaction kinetics equation, and the preservation rates decrease with the rise of temperature, but the temperature stability of anthocyanin microcapsule powder is higher than that of anthocyanin. The stabilities of anthocyanin microcapsules in the artificial simulated gastric and intestinal juice are higher than those of anthocyanin.

Embodiment 5

The present embodiment provides use of the anthocyanin microcapsule product obtained by the microencapsulation method in embodiment 4 in the preparation of food, healthcare products or food additives.

In conclusion, in the present invention, the microencapsulation method of anthocyanin is optimized by adopting the improved process parameters (including a ratio of sodium alginate to calcium carbonate to water, a ratio of sodium alginate to anthocyanin, a ratio of water phase to oil phase, a ratio of acidic solution to calcium carbonate, the mass concentration of NaCl, etc.) to ensure the structural stability of anthocyanin. Meanwhile, the optimized spray drying parameters are combined to significantly improve the light, temperature and gastric and intestinal digestion stabilities of anthocyanin microcapsules.

The equipment number and the treatment scale described here are used to simplify the illustration of the present invention. The application, modification and variation of the present invention will be apparent to those skilled in the art. In addition, the technical characteristics in the above embodiments 1-5 can be arbitrarily combined; and all the combined technical solutions shall belong to the protection scope of the present invention.

The implementation solutions of the present invention have been disclosed as above, but are not limited to the applications listed in the description and embodiments, and are applicable to various fields suitable for the present invention. For those skilled in the art, other modifications can be easily implemented. Therefore, the present invention is not limited to specific details and embodiments shown and described herein without departing from the general concepts defined by claims and equivalent scopes.

What is claimed is:

1. A microencapsulation method for improving stability of anthocyanins, comprising the following steps:
   S1, taking sodium alginate as a wall material, respectively preparing sodium alginate, calcium carbonate and water according to a weight ratio of sodium alginate to calcium carbonate to water of (2-4):1:(15-25), and then adding the sodium alginate and the calcium carbonate into water to swell for 1-2 h to obtain a wall material gel system;
   S2, taking anthocyanins as a core material, and fully and uniformly mixing the wall material gel system with an anthocyanin solution for later use at a weight ratio of the sodium alginate to the anthocyanins of (12-20):1 to obtain a water phase;
   S3, mixing sorbitan monooleate with vegetable oil at a volume ratio of (1-2):1 to obtain an oil phase, mixing the water phase with the oil phase at a volume ratio of (3-5):1, and magnetically stirring the mixture for emulsifying to obtain a W/O emulsion; and
   S4, adjusting the pH of the W/O emulsion to be acidic, mixing the W/O emulsion with a buffer solution at a volume ratio of 1:(3-5), standing for 1-2 h, and separating the oil phase from the water phase to obtain a liquid anthocyanin microcapsule.

2. The microencapsulation method according to claim 1, wherein in the step S1, the weight ratio of the sodium alginate to the calcium carbonate to the water is 3:1:20.

3. The microencapsulation method according to claim 1, wherein in the step S2, the weight ratio of the sodium alginate to the anthocyanins is 15:1.

4. The microencapsulation method according to claim 1, wherein in the step S3, the volume ratio of the water phase to the oil phase is 4:1.

5. The microencapsulation method according to claim 1, wherein in the step S4, the step of adjusting the pH of the W/O emulsion to be acidic comprises: adding the vegetable oil containing an acidic solution into the W/O emulsion, and a weight ratio of the acidic solution to calcium carbonate is 3:1.

6. The microencapsulation method according to claim 1, wherein in the step S4, the buffer solution is a phosphate buffer solution containing NaCl with a mass concentration of 0.9%.

7. The microencapsulation method according to claim 1, further comprising a step S5 of spray-drying the liquid anthocyanin microcapsule to obtain anthocyanin microcapsule powder under the conditions that the heater temperature is 100-130° C., the feed rate is 10-15 r/min, and the vacuum pressure is 0.02-0.05 MPa.

8. The microencapsulation method according to claim 7, wherein in the step S2, the anthocyanins are prepared by the following processes:
- S21, drying and crushing raw materials for extracting the anthocyanins, and sieving the obtained raw materials with a 200-300-mesh sieve to obtain raw material powder;
- S22, mixing the raw material powder with an extracting solution uniformly at a weight-volume ratio of 1:(15-20); then adding a compound enzyme accounting for 0.02-0.03% by weight of the raw material powder to obtain an extraction system; performing ultrasonic extraction at 35-45° C. in the extraction system for 60-90 min, wherein the extracting solution comprises 70-75% of ethanol with a volume fraction of 85%, 2-4% of acetic acid with a volume fraction of 5%, 10-12% of sucrose and 10-12% of choline chloride by weight, the ultrasonic power in the ultrasonic extraction is 200-400 W, the compound enzyme is composed of cellulase, pectinase and amylase based on weight parts and the weight ratio of the cellulase to the pectinase to the amylase is 1:1:1.5; and performing solid-liquid separation after the ultrasonic extraction to obtain a first filter residue and a first filtrate;
- S23, adding 85% ethanol and 3% citric acid solution, which are 5-8 times the weight of the first filter residue and 0.2-0.3 time the weight of the first filter residue respectively, into the first filter residue, performing ultrasonic extraction at 35-45° C. for 45-60 min, and performing solid-liquid separation after the ultrasonic extraction to obtain a second filter residue and a second filtrate;
- S24, combining the first filtrate with the second filtrate to obtain a crude extract, centrifuging the crude extract at 8000-10000 rpm for removing precipitates to obtain a refined extract, and sequentially filtering the refined extract through a microfiltration membrane with an aperture of 2-5 μm, an ultrafiltration membrane with an aperture of 0.02-0.05 μm and a nanofiltration membrane with an aperture of 0.001-0.002 μm to obtain an extracted clear solution, wherein the filtration pressure is 0.2-0.4 MPa and the filtration temperature is 25-35° C. when the refined extract is filtered through the microfiltration membrane with the aperture of 2-5 μm and the ultrafiltration membrane with the aperture of 0.02-0.05 μm; and the filtration pressure is 1.5-2.0 MPa and the filtration temperature is 25-35° C. when the refined extract is filtered through the nanofiltration membrane with the aperture of 0.001-0.002 μm;
- S25, adding 85% ethanol, which is 1-2 times the volume of the extracted clear solution, into the extracted clear solution, centrifuging at 12000 rpm for 15 min, making the supernatant obtained after discarding precipitates pass through a column filled with XAD-7HP macroporous adsorption resin, wherein a volume ratio of the supernatant to the column is 3:1, eluting the macroporous adsorption resin with 5% ethanol to remove impurities after the macroporous adsorption resin forms a saturated uniform color band, then desorbing a pigment adsorbed by the macroporous adsorption resin with 1-2 column volumes of 70% acidic ethanol until the macroporous adsorption resin is colorless, and collecting eluent;
- S26, concentrating the eluent by a high-pressure reverse osmosis membrane after passing through the ultrafiltration membrane with the aperture of 0.02-0.05 μm, to obtain an intercepted concentrated solution with a solid content of 15-25%, wherein the interception molecular weight of the high-pressure reverse osmosis membrane is 200 Da, the concentration temperature is 25-35° C., and the pressure is 3.0-4.5 MPa during concentration by the high-pressure reverse osmosis membrane;
- S27, concentrating the intercepted concentrated solution under vacuum and reduced pressure at 35-55° C. until ethanol is completely removed, to obtain a concentrated solution with a Baume degree of 3-5°; and
- S28, adding 10% acetic acid, which is 4-5% by volume of the concentrated solution, into the concentrated solution, heating at 30-40° C. for 30 min, rapidly freezing at −70° C., and then freeze-drying to obtain the anthocyanins.

* * * * *